United States Patent
Ruan

(10) Patent No.: US 10,442,799 B1
(45) Date of Patent: Oct. 15, 2019

(54) HETEROCYCLIC COMPOUNDS AND USES THEREOF

(71) Applicant: Fuqiang Ruan, Bellevue, WA (US)

(72) Inventor: Fuqiang Ruan, Bellevue, WA (US)

( * ) Notice: Subject to any disclaimer, the term of this patent is extended or adjusted under 35 U.S.C. 154(b) by 0 days.

(21) Appl. No.: 16/375,828

(22) Filed: Apr. 4, 2019

Related U.S. Application Data

(60) Provisional application No. 62/654,313, filed on Apr. 7, 2018.

(51) Int. Cl.
| | | |
|---|---|---|
| *C07D 413/14* | (2006.01) | |
| *C07D 401/14* | (2006.01) | |
| *C07D 471/04* | (2006.01) | |
| *A61P 35/00* | (2006.01) | |

(52) U.S. Cl.
CPC ......... *C07D 413/14* (2013.01); *C07D 401/14* (2013.01); *C07D 471/04* (2013.01); *A61P 35/00* (2018.01)

(58) Field of Classification Search
CPC .. C07D 413/04; C07D 401/14; C07D 471/04; A61P 35/00
See application file for complete search history.

(56) References Cited

U.S. PATENT DOCUMENTS

| | | | |
|---|---|---|---|
| 8,586,739 B2 | 11/2013 | Chen et al. | |
| 8,785,470 B2 | 7/2014 | Castro et al. | |
| 9,637,488 B2 | 5/2017 | Ruan | |
| 2014/0179673 A1* | 6/2014 | Evarts | C07D 471/08 514/210.21 |
| 2015/0148375 A1 | 5/2015 | Yue et al. | |
| 2015/0158873 A1 | 6/2015 | Bogdan et al. | |
| 2015/0315207 A1 | 11/2015 | Morales et al. | |
| 2017/0101418 A1 | 4/2017 | Durden et al. | |

FOREIGN PATENT DOCUMENTS

| | | |
|---|---|---|
| WO | 2005113556 A1 | 12/2005 |
| WO | 2008118454 A2 | 10/2008 |
| WO | 2008118455 A1 | 10/2008 |
| WO | 2008118468 A1 | 10/2008 |
| WO | 2009081105 A2 | 8/2009 |
| WO | 2010100405 A1 | 9/2010 |
| WO | 2012003271 A1 | 1/2012 |
| WO | 2013097601 A1 | 6/2013 |
| WO | 2013097601 A1 | 7/2013 |
| WO | 2014100765 A1 | 6/2014 |
| WO | 2014201409 A1 | 12/2014 |
| WO | 2014206150 A1 | 12/2014 |
| WO | 2015010641 A1 | 1/2015 |
| WO | 2015022332 A1 | 2/2015 |
| WO | 2016077378 A1 | 5/2016 |
| WO | 2016077380 A1 | 5/2016 |
| WO | 2016139361 A1 | 9/2016 |

OTHER PUBLICATIONS

Ahuja, P., et al., J Clin Invest. 2010; 120:1494-1505.
Ali, K., et al., Nature. 2014; 510:407-411.
Andrews, F.H., et al., Proc Natl Acad Sci USA. 2017; 114(7):E1072-E1080.
Andrieu, G., et al., Drug Discovery Today: Technol. 2016; 19:45-50.
Berge, S.M. et al., J. Pharm. Sci. (1977) 66:1-19.
Casey, S.C., et al., Blood. 2018; 131(18):2007-2015.
Ciceri, P., et al., Nat Chem Biol. 2014; 10(4):305-312.
Crawford, T.D., et al., J Med Chem. 2016; 59:5391-5402.
Dang, C.V., Cell. 2012; 149(1):22-35.
Dawson, M.A., et al., Nature. 2011; 478(7370):529-533.
Delmore, J.E., et al., Cell. 2011; 146(6):904-917.
Dey, N., et al., Am J Cancer Res. 2015; 5(1):1-19.
Dittmann, A., et al., ACS Chem. Biol. 2014; 9(2):495-502.
Eickholt, B.J., et al., PLoS One. 2007; 2(9):e869.
Eliel, E. and Wilen, S., Stereochemistry of Organic Compounds (1994) John Wiley & Sons, Inc., New York.
Ember, S.W., et al., ACS Chem Biol. 2014; 9(5):1160-1171.
Engelman, J.A., et al., Nat Rev Genet. 2006; 7(8):606-619.
Filippakopoulos, P., et al., Nature. 2010; 468(7327):1067-1073.
Foster, A.B., Trends Pharmacol. Sci. (1984) 5:524-527.
Fruman, D.A., et al., Nat Rev Drug Discov. 2014; 13(2):140-156.
Tomska, K., et al., Scientific Reports. 2018; 8(12046):1-11.
The Chemistry of Heterocyclic Compounds, a series of Monographs (John Wiley & Sons, New York, 1950 to present).
The Practice of Medicinal Chemistry (Camile G. Wermuth, Academia Press, 2003).
Weidner, A-S., et al., Am J Surg Pathol. 2015; 39:1661-1667.
Wu, S.Y., et al., J Bio Chem. 2007; 282:13141-13145.
Xiao, H.M., et al., Pharm Res. 2010; 27:739-749.
Yu, W., et al., J Med Chem. 2018; 61:3984-4003.
Zhang, G., et al., Chem Rev. 2015; 115(21):11625-11668.
Zhang, G., et al., J Med Chem. 2013; 56(22):9251-9264.
Zhao, L., et al., J Med Chem. 2015; 58(3):1281-1297.
Gamberi G., et al., Oncology. 1998; 55:556-563.
Greene T.W., et al., Protective Groups in Organic Synthesis, 3rd edition (1999) John Wiley & Sons.
Haynes, D.A. et al., J. Pharm. Sci. (2005) 94:2111-2120.
Higuchi et al., Pro-drugs as Novel Delivery Systems, vol. 14 of the A.C.S. Symposium Series.
Klempner, S.J., et al., Cancer Discovery. 2013; 3:1345-1354.
Kok, K., et al., Trends Biochem. Sci. 2009; 34:115-127.
Kurimchak, A.M., et al., Cell Reports. 2016; 16:1273-1286.
Liu, P., et al., Nat Rev Drug Discov. 2009; 8(8):627-644.
March's Advanced Organic Chemistry (Michael B. Smith & Jerry March, Wiley-Interscience (2000).
Martin, L.J., et al., J Med Chem, 2016; 59:4462-4475.
Mertz, J.A., et al., Proc Natl Acad Sci U S A. 2011; 108:16669-16674.
Modern Pharmaceutics, Marcel Dekker, Inc. 3rd Ed. (G.S. Banker & C.T. Rhodes, Eds.).
Nair S.K., et al., Cell. 2003; 112:193-205.
Nesbit C.E., et al., Oncogene. 1999; 18:3004-3016.
Pap, T., et al., Arthritis Rheum. 2004; 50:2794-2802.

(Continued)

*Primary Examiner* — Timothy R Rozof

(57) ABSTRACT

In recognition of the unmet need to develop novel therapeutic agents, the present invention discloses a novel class of heterocycles as dual inhibitors of BRD4 and class I PI3Ks. The compounds claimed herein could be used alone or in combination therapies for the effective treatment of a wide range of age-related diseases, including cancer. The present invention also provides methods for preparing compounds of the invention thereto.

3 Claims, No Drawings

(56) References Cited

OTHER PUBLICATIONS

Paquette, L.A., Principles of Modern Heterocyclic Chemistry (W. A. Benjamin, New York, 1968), particularly Chapters 1, 3, 4, 6, 7, and 9.
Parker, S.P., Ed., McGraw-Hill Dictionary of Chemical Terms (1984) McGraw-Hill Book Company, New York.
Picaud, S., et al., Cancer Res. 2015; 75(23):5106-5119.
Prochownik, E.V., et al., Genes Cancer. 2010; 1(6):650-659.
Puissant, A., Cancer Discov. 2013; 3(3):308-323.
Ran, X., et al., J Med Chem. 2015; 58(12):4927-4939.
Remington's Pharmaceutical Sciences, 18th Ed., Mack Publishing Co, Easton, PA., 1990.
Roche (ed.),Bioreversible Carriers in Drug Design, American Pharmaceutical Association and Pergamon Press (1987), Chapter 1, pp. 1-12.
Sander, S., et al., Cancer Cell. 2012; 22(2):167-179.
Schmid, M.C., et al., Cancer Cell. 2011; 19:715-727.
Schmitz, R., et al., Nature. 2012; 490:116-120.
Shepherd, C., et al., Leukemia. 2013; 27(3):650-660.
Sipos, F., et al., World Journal of Gastroenterology. 2016; 22 (35):7938-7950.
Talevi, A., Front Pharmacol. 2015; 6:205.
Tinsley, S., et al., Br J Haematol. 2015; 170:275-278.

\* cited by examiner

HETEROCYCLIC COMPOUNDS AND USES THEREOF

CROSS-REFERENCE TO RELATED APPLICATION

This application claims the benefit of priority to U.S. provisional patent application Ser. No. 62/654,313, filed Apr. 7, 2018, which is hereby incorporated by reference.

FIELD OF THE INVENTION

The present invention relates generally to MYC, phosphatidylinositol 3-kinases (PI3Ks) and BET bromodomain-containing proteins (BRDs), and more specifically to novel dual inhibitors of class I PI3Ks and BRD4, and methods of, making and using such inhibitors.

BACKGROUND OF THE INVENTION

MYC (v-myc myelocytomatosis viral oncogene homolog) is a pleiotropic transcription factor that regulates a variety of functions by promoting activation or repression of genes on a global scale, and plays a central role in the pathophysiology of cancer, inflammation, and heart disease.

The overexpression of MYC is common in many types of human cancer. Tumors can employ multiple genetic and epigenetic mechanisms to upregulate MYC, and such amplification or overexpression is often correlated with a poor clinical outcome, aggressive biological behavior, increased likelihood of relapse, and advanced stage of disease (Gamberi G., et al., Oncology. 1998; 55:556-563; Nesbit C. E., et al, Oncogene. 1999; 18:3004-3016). Recently, MYC expression in tumor cells has also been shown to regulate the tumor microenvironment through effects on both innate and adaptive immune effector cells and immune regulatory cytokines, and MYC inactivation can restore the immune response against a tumor (Casey, S. C., et al., Blood. 2018; 131(18): 2007-2015). Beyond cancer, MYC gene is frequently deregulated in tissue inflammation, and its overexpression or activation has been observed in both sporadic and colitis-associated colon adenocarcinomas and in disease conditions such as rheumatoid arthritis (Sipos, F., et al., World Journal of Gastroenterology. 2016; 22(35):7938-7950; Pap, T., et al., Arthritis Rheum. 2004; 50:2794-2802). MYC function has also been implicated in the pathophysiology of heart failure during tissue remodeling associated with hypertrophy and, dilatation (Ahuja, P., et al., J Clin Invest. 2010; 120:1494-1505). Thus, MYC is an appealing target for discovery and development of therapeutics. To date, despite unmet medical needs, small molecule inhibitors of MYC have remained elusive, and MYC has thus far proven undruggable (Prochownik, E. V., et al., Genes Cancer. 2010; 1(6):650-659; Nair, S. K., et al., Cell. 2003; 112:193-205).

Increasing evidence suggests that targeting upstream MYC regulators may be an effective strategy to suppress MYC. One of such strategies is to inhibit bromo and extra-terminal (BET) bromodomain proteins such as bromodomain-containing protein 4 (BRD4), which are transcriptional regulators that are required for the efficient expression of MYC (Delmore, J. E., et al, Cell 2011; 146(6):904-917; Mertz, J. A., et al, Proc Natl Aced Sci USA. 2011; 108:16669-16674; Puissant, A., Cancer Discov. 2013; 3(3):308-323). The bromodomain (BRD) family of proteins is a class of epigenetic readers that recognize acetyllysine (KAc) residues of histones. The binding interaction between BRDs and histones creates a scaffold for the assembly of protein complexes that alter chromatin accessibility to transcription factors and allows the recruitment or activation of RNA polymerases, leading to regulation of gene transcription and/or chromatin remodeling. BET bromodomain inhibition exerts a broad spectrum of desired biological effects such as anticancer, anti-inflammatory properties. BRD4 is ubiquitously expressed and contains two highly conserved N-terminal bromodomains (BD1 and BD2), an ET domain, and a C-terminal domain. BRD4 (BD1) and BRD4 (BD2) interact with acetylated chromatin as well as nonhistone proteins to regulate transcription, DNA replication, cell cycle progression, and other cellular activities (Wu, S. Y., et al., J Bio Chem. 2007; 282:13141-13145). Most BRD4 inhibitors block the interactions between BRD4 and acetyl-lysine by mimicking acetyl-lysine and competing with it to bind BRD4.

Targeting MYC function via BET bromodomain inhibition has now been validated by studies in Burkitt lymphoma, B- and T-cell acute lymphoblastic leukemia, non-small-cell lung carcinoma, diffuse large B-cell lymphoma, and neuroblastoma (Filippakopoulos, P., et al., Nature. 2010; 468 (7327)1067-1073; Zhang, G., et al, Chem Rev. 2015; 115 (21):11625-11668; Delmore J. E., et al., Cell. 2011; 146(6): 904-917; Dawson, M. A., et al., Nature. 2011; 478:529-533; Puissant, A., et al., Cancer Discov. 2013; 3(3):308-323; Ran, X., et al., J Med Chem. 2015; 58(12):4927-4939; Zhang, a, et al., J Med Chem. 2013; 56(22):9251-9264; Zhao, L., et al., J Med Chem. 2015: 58(3)1281-1297; Picaud, S., et al., Cancer Res. 2015; 75(23):5106-5119). To date, at least seven BET bromodomain inhibitors are in active clinical trials for cancer (Andrieu, G., et al., Drug Discovery Today: Technol. 2016; 19:45-50), but none has received FDA approval.

Although BET bromodomain inhibitors show great promise as cancer therapeutics, emerging studies have shown that cancer cells can acquire resistance to inhibition of BET bromodomain, indicating that single-agent therapies targeting BRD4 may not provide durable therapeutic response. Resistance to BET bromodomain inhibitors is mediated by adaptive kinome reprogramming, and co-targeting BET bromodomain proteins and receptor tyrosine kinases (RTKs) and/or phosphatidylinositol 3-kinase (PI3K) signaling may be required to maximize clinical benefit (Kurimchak, A. M., et al., Cell Reports. 2016; 16:1273-1286).

The PI3K signaling pathway, defined by PI3K, AKT (serine/threonine kinase) and mTOR (mammalian target of rapamycin), is one of the key signaling networks in cancer cell initiation, growth, proliferation, and survival (Engelman, J. A., et al., Nat Rev Genet. 2006; 7(8):606-619; Liu, P., et al., Nat Rev Drug Discov. 2009; 8(8):627-644). Blockade of the PI3K pathway has also been shown to suppress MYC activity by inhibiting MYC gene transcription (Dey, N., et al., Am J Cancer Res. 2015; 5:1-19) and decreasing MYC protein stability, and PI3K inhibition potentiates MYC down-regulation and cell death in MYC-dependent NMC cells (Tinsley, S., et al., Br J Haematol. 2015; 170;275-278).

The main PI3-kinase isoforms in cancer are class I PI3Ks, designated PI3K α, β, δ, and γ, each comprising a 110 kDa catalytic subunit and a smaller associated regulatory subunit. Class Ia PI3Ks (α, β, and δ) containing the catalytic subunits p110α, p110β, and p110δ, respectively, are activated through tyrosine kinase signaling. In contrast, the sole class Ib member, PI3Kγ, contains catalytic subunit p110γ associated with either a p101 or p84 regulatory subunit, and is mostly activated through GPCRs. While PI3Kα and PI3Kβ are ubiquitously expressed, and the dysregulation of PI3Kα and PI3Kβ is implicated in the etiology of solid tumors.

PI3Kδ and PI3Kγ are found in leukocytes (B and T cells, and myeloid lineage cells) with PI3Kδ nearly confined to spleen, thymus, and peripheral blood leukocytes (Eickholt, B. J., et al., PLoS One. 2007; 2(9):e869; Kok, K., et al., Trends Biochem. Sci. 2009; 34:115-127), and the dysregulation of P13 .6 and PI3Kγ has been implicated in diseases of the innate and, adaptive immune system such as rheumatoid arthritis (RA), systemic lupus erythematosus (SLE), and hematological malignancies. PI3Kγ inhibition breaks the regulatory checkpoint in T cells in a wide range of solid tumours, and the blockade of PI3Kγ in myeloid cells suppress inflammation, growth and metastasis of tumours (Ali, K., et al., Nature. 2014; 510:407-411; Schmid, M. C., et al., Cancer Cell. 2011; 19:715-727); however, like immune checkpoint inhibitors, idelalisib, the first p110δ-selective inhibitor approved by FDA, has immune-related toxicity in the gastrointestinal tract (Weidner, A-S., et al., Am J Surg Pathol. 2015; 39:1661-1667).

Abundant evidence has also revealed that the PI3K pathway is, frequently mutated or altered in numerous forms of human cancers (e.g., breast tumors), and emerging clinical data show limited single-agent activity of over 30 clinical candidates targeting, the PI3K pathway at tolerated doses in solid tumors with an accompanied rapid emergence of drug resistance (Liu, P., et al., Nat Rev Drug Discov. 2009; 8(8):627-644; https://clinicaltrials.gov/; Dey, N., et al., Am J Cancer Res. 2015; 5(1):1-19; Fruman, D. A., et al., Nat Rev Drug Discov. 2014; 13(2):140-156). It is clear that there is an unmet need for novel second-generation PI3K inhibitors with improved efficacy and more durable responses over existing drugs in order to overcome the limitation of PI3K inhibition in the treatment of heterogeneous and drug-resistant tumors; there is also an unmet need for developing more efficacious drugs with improved tolerability to treat MYC-driven and PI3K-related cancer.

It is evidenced that PI3Ks and MYC form interlinked but overlapping signaling pathways (Gang, C. V., Cell. 2012; 149(1):22-35). Both pathways are often dysregulated cooperatively in hematopoietic malignancies, and in patients with Burkitt lymphoma as well as in a mouse model of the disease (Sander, S., et al., Cancer Cell. 2012; 22(2):167-179; Schmitz, R., et al., Nature. 2012; 490:116-120). MYC upregulation can impair the response to PI3K inhibitors and is an important mechanism underlying tumor resistance to PI3K pathway inhibition (Klempner, S. J., et al., Cancer Discovery. 2013; 3:1345-1354; Shepherd, C., et al., Leukemia. 2013; 27(3):650-660). Recently, drug-based perturbation screen uncovers that idelalisib was synergistic when combined with BET inhibitors such as JQ1 and OTX015, and, more importantly, synergy for OTX015 with idelalisib at concentrations in vitro observed can be safely administrated in the clinical setting in vivo (Tomska, K., et al., Scientific Reports. 2018; 8:12046). Thus, co-targeting both PI3K and BRD4 could be a rational and sensible combination strategy.

The "multi-targeted or dual-targeted single agent" therapeutic strategy is well-established and, in principle, could confer the same benefits as combination therapies without major clinical development challenges and high treatment costs (Talevi, A., Front Pharmacol. 2015; 6:205). To date, many multitarget drugs have been approved or are in advanced development stages, and many dual kinase-bromodomain inhibitors have been identified from known kinase inhibitors (Xiao, H. M., <et al., Pharm Res. 2010; 27:739-749; Ciceri, P., et al., Nat'Chem Biol. 2014; 10(4): 305-312; Ember, S. W., et al., ACS Chem Biol. 2014; 9(5):1160-1171). However, dual PI3-kinase and bromodomain inhibitors are rare (Dittmann, A., et al., ACS Chem. Biol. 2014; 9(2):495-502; US 20150315207/US 20170101418). A dual inhibitor of PI3K-BRD4 blocks cancer cell growth and metastasis via the orthogonal inhibition of MYC, and is less toxic to the host organism in vivo than a combination of an equipotent PI3K inhibitor and BRD4 inhibitor (Andrews, F. H., et al., Proc Natl Acad Sci USA. 2017; 114(7):E1072-E1080).

It is clear that there is an unmet need for therapeutically effective inhibitors with improved tolerability over existing drugs, there is an unmet need for small molecules co-targeting both PI3K signaling pathway and bromodomain proteins such as BRD4. The present invention provides such compounds as further described below.

SUMMARY OF THE INVENTION

The present invention provides the compounds having the structure:

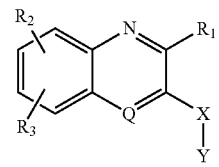

or stereoisomers, geometric isomers, tautomers, solvates (e.g., hydrate), metabolites, prodrugs, isotopically-labeled derivates, and any pharmaceutically acceptable salts thereof, wherein:

X is selected from:

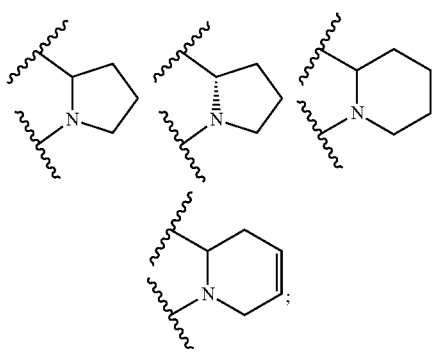

Q is C or N;

$R_1$ is selected from: a direct-bonded, or —NH-linked, or —NH$C_1$-$C_3$ alkyl linked aryl, heteroaryl, cycloalkyl, heterocycloalkyl, or a nitrogen-bonded cycloalkyl, heterocycloalkyl, or —NH$C_1$-$C_4$ alkyl, —N($C_1$-$C_4$ alkyl)$_2$, each of which is substituted by 0-4 substituents optionally selected from a group of hydrogen, deuterium, halogen, $C_1$-$C_4$ alkyl, $C_1$-$C_3$ haloalkyl, —OH, —O$C_1$-$C_6$ alkyl, —O$C_1$-$C_6$ alkyl—C(O)NH-OH, —NH$_2$, —C(O)NH—$C_1$-$C_6$ alkyl-heteroaryl, —NHC(O)$C_1$-$C_6$ alkyl—C(O)NH—OH, or heteroaryl;

In one embodiment, $R_1$ is phenyl, 5- and 6-membered heteroaryl containing 1, or 2 atoms selected from N, O, S, but containing no more than one O or S, each of which is substituted by 0-4 substituents optionally selected from a group of hydrogen, deuterium, halogen, $C_1$-$C_4$ alkyl, $C_1$-$C_3$ haloalkyl, —OH, —O$C_1$-$C_6$ alkyl, —O$C_1$-$C_6$ alkyl—C(O)

NH—OH, —NH$_2$, —C(O)NH— C$_1$-C$_6$ alkyl-heteroaryl, —NHC(O)C$_1$-C$_6$ alkyl—C(O)NH—OH, or heteroaryl;

In one embodiment, R$_1$ is —NHC$_1$-C$_4$ alkyl, —N(C$_1$-C$_4$ alkyl)$_2$, or a direct bonded or nitrogen-bonded or —NHC$_1$-C$_3$ alkyl linked 3- to 7-membered monocyclic ring containing 0, 1, or 2 atoms selected from N, O, S, but containing no more than one O or S, wherein the available carbon atoms of the ring is unsubstituted or substituted by one or two substituents, optionally selected from a group of hydrogen, deuterium, halogen, C$_1$-C$_4$ alkyl, C$_1$-C$_3$ haloalkyl, —OH, —OC$_1$-C$_6$ alkyl, —OC$_1$-C$_6$ alkyl—C(O)NH—OH, —C(O)NH— C$_1$-C$_6$ alkyl-heteroaryl, —NHC(O)C$_1$-C$_6$ alkyl—C(O)NH—OH, or heteroaryl;

R$_2$ is a acetyl-lysine (KAc)-mimicking group; in a preferred embodiment, R$_2$ is selected from:

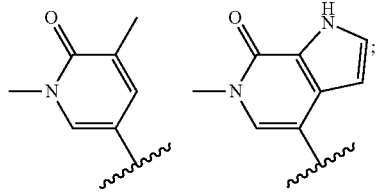

R$_3$ is independently selected from: hydrogen, deuterium, small alkyl, methoxy, halogen; in a preferred embodiment, R$_3$ is hydrogen, or deuterium;

Y is selected from an optionally substituted mono-or bicyclic heteroaryl group containing at least one nitrogen atom. In a preferred embodiment, Y is selected from:

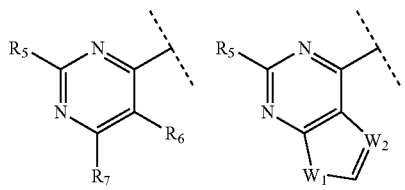

wherein:

R$_5$ is independently selected from H, NH$_2$, CN, CONH$_2$, halogen;

R$_6$ is independently selected from H, CH$_3$, CN, halogen, trifluoromethyl, difluoromethyl, trideuteromethyl, amino, or an unsubstituted or substituted 5- to 6-membered heteroaryl, or -ethynylheteroaryl;

R$_7$ is selected from: H, NH$_2$;

W$_1$ is independently selected from NH, NCH$_3$ or S;

W$_2$ is independently selected from N, C-H, C-D, C-F, or C—CH$_3$.

In some embodiments, the compounds are the atropisomers. In other embodiments, the compounds are the (S)-enantiomer. In some other embodiments, the compounds are the (R)-enantiomer.

Another aspect of the present invention is to provide the compounds having the structure:

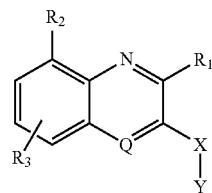

or stereoisomers, geometric isomers, tautomers, solvates (e.g., hydrate), metabolites, prodrugs, isotopically-labeled derivates, and pharmaceutically acceptable salts thereof; wherein R$_1$, R$_2$, R$_3$, Q, X, and Y are as defined above.

Another aspect of the present invention is to provide the compounds having the structure:

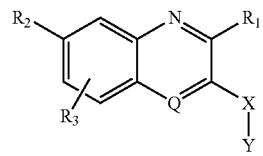

or stereoisomers, geometric isomers, tautomers, solvates (e.g., hydrate), metabolites, prodrugs, isotopically-labeled derivates, and pharmaceutically acceptable salts thereof; wherein R$_1$, R$_2$, R$_3$, Q, X, and Y are as defined above.

Another aspect of the present invention is to provide the compounds having the structure:

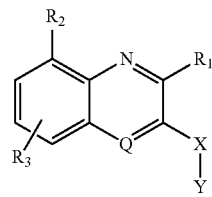

or stereoisomers, geometric isomers, tautomers, solvates (e.g., hydrate), metabolites, prdrugs, isotopically-labeled derivates, and pharmaceutically acceptable salts thereof, wherein:

R$_2$, R$_3$, Q, and Y are as defined above;

X is:

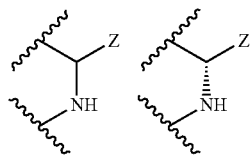

Wherein: Z is hydrogen, or CH$_3$, or small alkyl;

R$_1$ is selected from: —NHC$_1$-C$_4$ alkyl , —N(C$_1$-C$_4$ alkyl)$_2$, or a direct bonded or nitrogen-bonded or —NHC$_1$-C$_3$ alkyl linked 3- to 7-membered monocyclic ring containing 0, 1, or 2 atoms selected from N, O, S, but containing no more than one O or S, wherein the available carbon atoms of the ring is unsubstituted or substituted by one or two substituents, optionally selected from a group of hydrogen, deuterium, halogen, C$_1$-C$_4$ alkyl, C$_1$-C$_3$ haloalkyl, —OH, —OC$_1$-C$_6$ alkyl, —OC$_1$-C$_6$ alkyl—C(O)NH—OH, —NH$_2$, —C(O)NH— C$_1$-C$_6$ alkyl-heteroaryl, —NHC(O)C$_1$-C$_6$ alkyl—C(O)NH—OH, or heteroaryl.

Another aspect of the present invention is to provide the compounds having the structure:

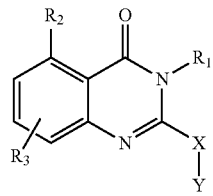

or stereoisomers, geometric isomers, tautomers, solvates (e.g., hydrate), metabolites, prdrugs, isotopically-labeled derivates, and pharmaceutically acceptable salts thereof, wherein:

R$_3$ and Y are as defined above;
X is:

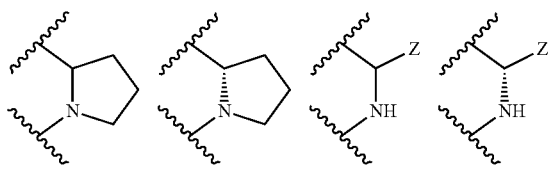

Wherein: Z is hydrogen, or CH$_3$, or small alkyl;
R$_2$ is selected from:

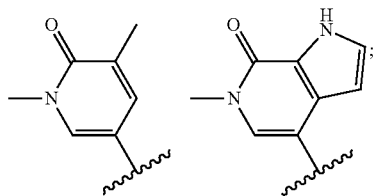

R$_1$ is selected from:

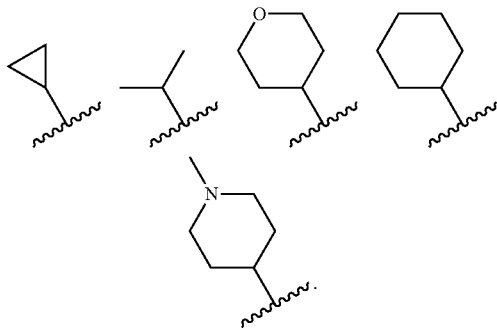

Another aspect of the present invention is to provide compounds that, inhibit class I PI3Ks, inhibit BRDs, and co-inhibit class I PI3Ks and BRDs. This invention indentifies potent compounds that are useful for medical treatment of diseases mediated or driven by human MYC and/or BRDs and/or PI3Ks dysfunction, including, but not limited to, proliferative diseases such as cancer and/or relapsed cancer.

Preferred compounds of the present invention possess an IC$_{50}$ value for the inhibition of class I PI3Ks, BRDs of less than 10 μM, preferably less than 1 μM, even more preferably less than 0.1 μM in a biochemical assay. The compounds are readily synthesized and can be administered to patients by a variety of methods.

Compounds of the present invention may contain chiral centers and therefore may exist in different enantiomeric and diastereomeric forms. This invention relates to all optical isomers and all stereoisomers of compounds having the structures as defined above, both as racemic mixtures and as individual enantiomers and diastereoismers of such compounds, and mixtures thereof, and to all pharmaceutical compositions and methods of treatment defined below that contain or employ them, respectively.

As the compounds of the present invention may possess at least two asymmetric centers, they are capable of occurring in various stereoisomeric forms or configurations. Hence, the compounds can exist in separated (+)- and (−)-optically active forms, as well as mixtures thereof. The present invention includes all such forms within its scope. Individual isomers can be obtained by known methods, such as optical resolution, optically selective reaction, or chromatographic separation in the preparation of the final product or its intermediate.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds". John Wiley & Sons, Inc., New York, 1994. The term "stereoisomers" refers to compounds which have identical chemical constitution, but differ with regard to the arrangement of the atoms or groups in space. "Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography. "Enantiomers" refer to two stereoisomers of a compound which are non-superimposable mirror images of one another.

The compounds of the present invention can exist in unsolvated forms as well as solvated forms, including hydrated forms. In general, the solvated forms, including hydrated forms, are equivalent to unsolvated forms and are intended to be encompassed within the scope of the present invention. A "solvate" refers to an association or complex of one or more solvent molecules and a compound of the present invention. Examples of solvents that form solvates include, but are not limited to, water, isopropanol, ethanol, methanol, DMSO, ethylacetate, acetic acid, and ethanolamine.

A "metabolite" is a product produced through metabolism in the body of a specified compound or salt thereof. Metabolites of a compound may be identified using routine techniques known in the art and their activities determined using tests such as those described herein. Such products may result e.g. from the oxidation, reduction, hydrolysis, amidation, deamidation, esterification, deesterification, enzymatic cleavage, and the like, of the administered compound. Accordingly, the present invention includes metabolites of compounds of the invention, including compounds produced by a process comprising contacting a compound of this invention with a mammal for a period of time sufficient to yield a metabolic product thereof.

The present invention also includes isotopically labeled compounds, which are identical to those recited in the present invention, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention described herein or pharmaceutically acceptable salts, tautomers, isomers, prodrugs, or solvates of said compounds or of said prodrugs which contain the aforementioned, isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. In addition, it is known that the deuterium atom ($^2H$) is a non-radioactive isotope of the hydrogen atom. Such compounds may increase resistance to metabolism, and thus may be useful for increasing the half-life of the compounds of the present invention or pharmaceutically acceptable salts, isomers, prodrugs, or solvates thereof, when administered to a mammal (see: e.g., Foster, A. B., Trends Pharmacol. Sci. 1984; 5(12): 524-527). Isotopically labeled compounds of this invention can generally be prepared by carrying out the procedures disclosed in the Examples of Preparations below, by substituting a readily available isotopically labeled reagent for a non-isotopically labeled reagent.

The terms "compound of this invention", and "compounds of the present invention" include compounds having the structure disclosed herein and stereoisomers, geometric isomers, tautomers, solvates, metabolites, isotopically labeled derivates, pharmaceutically acceptable salts and, prodrugs thereof.

The compounds of this invention are capable of further forming pharmaceutically acceptable formulations comprising salts, including but not limited to acid addition and/or base salts, solvents and N-oxides of a compound having the structure disclosed herein.

This invention also provides pharmaceutical formulations comprising a therapeutically effective amount of a compound having the structure disclosed herein or a therapeutically acceptable salt thereof and a pharmaceutically acceptable carrier, diluent, or excipient therefor. All of these forms are within the present invention.

As used herein, the term "alkyl" in the, present invention is, defined as linear or branched hydrocarbon groups containing the indicated number of carbon atoms and includes, for example, methyl, ethyl, n-propyl, isopropyl, n-butyl, sec-butyl, iso-butyl, tert-butyl, n-pentyl, iso-pentyl, n-hexyl, and the like.

The term "cycloalkyl" refers to a monovalent non-aromatic, saturated or partially unsaturated ring having 3 to 7 carbon atoms as a monocyclic ring or 7 to 12 carbon atoms as a bicyclic ring. Bicyclic ring having 7 to 12 atoms can be arranged, e.g., as a bicyclo[4,5], [5,5], [5,6] or [6,6] system, and bicyclic ring having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic ring include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, and the like.

By "Aryl" means an aromatic carbocyclic group having a single ring (e.g., phenyl), multiple rings (e.g., biphenyl), or multiple condensed rings in which at least one is aromatic. Aryl groups are optionally substituted independently with one or more substituents.

The terms "heterocycloalkyl", or "heterocyclic ring" are used interchangeably herein and similarly as cycloalkyl except the ring contains one or more heteroatoms selected from nitrogen, oxygen, phosphorus and sulfur, the remaining ring atoms being C, where one or more ring atoms is optionally substituted independently with one or more substituents described herein. A heterocyclic ring may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), e.g., a bicyclo[4,5], [5,5], [5,6], or [6,6] system. Heterocycles are described in Paquette, Leo A.; "Principles of Modem Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28. "heterocycloalkyl " also includes heterocycles that are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Examples of heterocyclic ring-based analogues also include, but are not limited to:

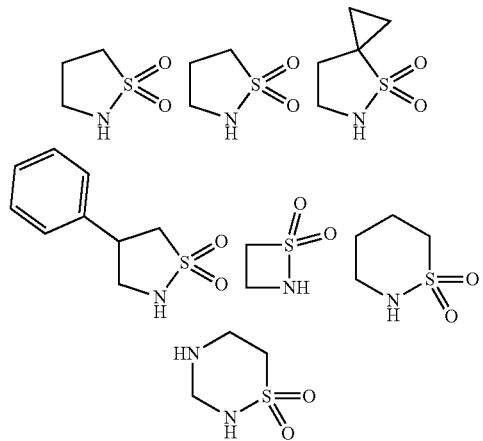

Spiro moieties, and bioisosteres are also included within the scope of this definition. For example, morpholine-based analogues include:

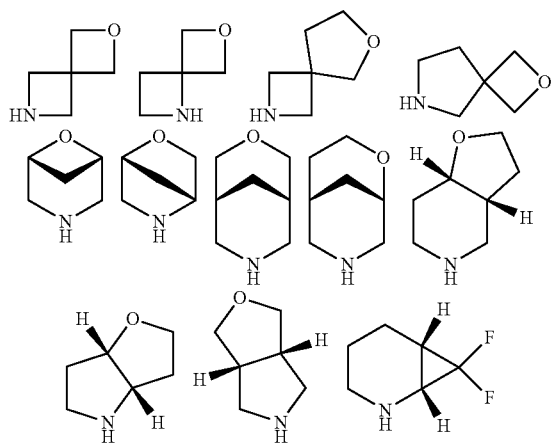

Examples of a heterocyclic group wherein 2 ring carbon atoms are substituted with oxo moieties are pyrimidinonyl and 1,1-dioxo-thiomorpholinyl. The heterocycle groups herein are optionally substituted independently with one or more substituents described herein.

The term "heteroaryl" is meant one or more aromatic ring systems of 5-, 6-, or 7-membered rings containing one or more heteroatoms independently selected from nitrogen, oxygen, and sulfur. Examples of heteroaryl groups are pyridinyl (including, e.g., 2-hydroxypyridinyl), imidazolyl, imidazopyridinyl, pyrimidinyl (including, e.g., 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoine, 1H-indazole, position 2 of a isoindole, or isoindoline, position 4 of a morpholine, and position 9 of a carbazole, or .beta.-carboline.

The term "halo" or "halogen" is defined as fluoro, bromo, chloro, and iodo.

The term "optionally selected" means that any one or more hydrogen atoms on the designated atom or group may or may not be replaced by a moiety other than hydrogen.

The term "pharmaceutically acceptable salt", as used herein, refers to pharmaceutically acceptable organic or inorganic salts or zwitterionic forms of a compound of the invention. The phrase "pharmaceutically acceptable" indicates that the substance or composition must be compatible chemically and/or toxicologically, with the other ingredients comprising a formulation, and/or the mammal being treated therewith. The salts can be prepared in situ during the final isolation and purification of the compound of the invention or by separately reacting the purified compound in its free base form with a suitable organic or inorganic acid. Various pharmaceutically acceptable salts are well known in the art (see: Berge S M et al., "Pharmaceutical Salts." J. Pharm. Sci. 1977; 66:1-19, and Haynes D A et al., "Occurrence of pharmaceutically acceptable anions and cations in the Cambridge Structural Database," J. Pharm. Sci. 2005; 94:2111-2120, which are hereby, incorporated herein by reference). For example, the list of FDA-approved commercially marketed salts includes acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, mitrate, pamoate, pantothenate, phosphate, diphosphate, polygalacturonate, salicylate, stearate, subacetate, succinate, sulfate, tannate, tartrate, teoclate, and triethiodide. Pharmaceutically acceptable salts of compounds of the invention generally are preferred in the methods of the present invention.

The term "prodrug" as used herein refers to compounds that are rapidly transformed in vivo to yield a compound having structure as defined herein, for example, by hydrolysis in, blood. A thorough discussion is provided in Higuchi et al, Pro-drugs as Novel Delivery Systems, Vol. 14 of the A.C.S. Symposium Series, and in Roche (ed.),"Bioreversible Carriers in Drug Design", American Pharmaceutical Association and Pergamon Press, (1987), both of which are hereby incorporated by reference. Prodrugs can be converted into a pharmacologically active form through hydrolysis of, for example, an ester or amide linkage, thereby introducing or exposing a functional group on the resultant product. Prodrugs can be designed to react with an endogenous compound to form a water-soluble conjugate that further enhances the pharmacological properties, of the compound, for example, increased circulatory half-life. Alternatively, prodrugs can be designed to undergo covalent modification on a functional group with, for example, glucuronic acid, sulfate, glutathione, amino acids, acetate, chemotherapeutic hormonal or antibody agents. The resulting conjugate can be inactivated and excreted in the urine, or rendered, more potent than the parent compound. High molecular weight conjugates also can be excreted into the bile, subjected to enzymatic cleavage, and released back into the circulation, thereby effectively increasing the biological half-life of the originally administered compound.

Another aspect of the invention is to provide a method for specifically inhibiting human class I PI3Ks' and/or BRDs' activity therapeutically or prophylactically, and, thereby promote medical treatment of diseases driven or mediated by human MYC and/or BRDs and/or class I PI3Ks dysfunction, comprising administering to a mammal (e.g., human) in need of such treatment an effective amount of a compound having the structure defined herein. In some embodiments, the disease or condition is MYC-dependent. In some embodiments, the disease or condition may be associated or mediated by PI3kδ and/or PI3Kγ activities. In certain embodiments, the disease or condition is associated or mediated by PI3Ks. In certain embodiments, the disease or condition is associated or mediated by BRDs. In some embodiments, the disease or condition is an inflammatory disorder, an autoimmune disease, or a cancer. In certain other embodiments, the disease or condition is type I and/or type II diabetes. In other embodiments, the disease or condition is an autoimmune disease. In additional embodiments, the disease or condition is a cancer, a relapsed cancer after treatment with chemotherapy, and a solid tumor. In additional embodiments, the disease or condition is related to excessive or destructive immune reactions, such as asthma, rheumatoid arthritis, multiple sclerosis, lupus, psoriasis, or chronic obstructive pulmonary disease (COPD). In other embodiments, the disease or condition is related to bone disorder, inflammatory disease, immune disease, nervous system disease (e.g., a neuropsychiatric disorder), metabolic disease, respiratory disease, thrombosis, and cardiac disease. In other embodiments, the disease or condition is sepsis or viral infection or AIDS.

Another aspect of the present invention provides methods of preventing or treating a hyperproliferative disorder and/or non-cancer proliferative disease, comprising administering to a mammal in need of such treatment an effective amount of a compound of the present invention, alone or in combination with one or more additional compounds having anti-hyperproliferative properties. Examples of such hyperproliferative disease or disorder include, but are not limited to, cancer and/or relapsed cancer after treatment with chemotherapy. In certain embodiment, the cancer or relapsed cancer after treatment with chemotherapy is lymphoma, leukemia, or solid tumor. The solid tumor is selected from the group consisting of pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors, bone cancer, and soft tissue sarcoma. In some embodiments, the solid tumor is from non-small cell lung cancer, small cell lung, cancer, colon cancer, CNS cancer, melanoma, ovarian cancer, renal cancer, prostate cancer, or breast cancer.

The term "treating", as used herein, refers to reversing, alleviating, inhibiting the progress of, or preventing the disorder or condition to which such term applies, or preventing one or more symptoms of such condition or disorder. The term "treatment", as used herein, refers to the act of treating, as "treating" is defined immediately above.

"Inflammatory disorder" as used herein refers to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis. "Inflammation" as used herein refers to a localized, protective response elicited by injury or destruction of tissues, which serves to destroy, dilute, or wall off (sequester) both the injurious agent and the injured tissue. Inflammation is associated with an influx of leukocytes and/or neutrophil chemtaxis. Inflammation can result from infection with pathogenic organisms and viruses, and from noninfectious means such as trauma or reperfusion following myocardial infarction or stroke, immune response to foreign antigen, and autoimmune responses. Accordingly, inflammatory disorders amenable to the invention encompass disorders associated with reactions of the specific defense system (i.e., the component of the immune system that reacts to the presence of specific antigens) as well as with reactions of the nonspecific defense system (e.g., granulocytes, and macrophages). In certain embodiments, the inflammatory disease or the immune disease is selected from asthma, emphysema, allergy, dermatitis, rheumatoid arthritis, psoriasis, lupus erythematosus, graft versus host disease, inflammatory bowel disease, eczema, scleroderma, Crohn's disease, or multiple sclerosis.

"Autoimmune disease" as used herein refers to any group of disorders in which tissue injury is associated with humoral or cell-mediated responses to the body's own constituents, In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), Sjoegren's syndrome, or autoimmune hemolytic anemia. "Allergic disease" as used herein refers to any symptoms, tissue damage, or loss of tissue function resulting from allergy.

The terms "cancer" refers to or describes the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulvar cancer, thyroid cancer, hepatic carcinoma, anal carcinoma, penile carcinoma, as well as head and neck cancer. More particular examples of such cancers include Burkitt, lymphoma, B- and T-cell acute lymphoblastic leukemia non-small-cell lung carcinoma, diffuse large B-cell lymphoma, and neuroblastoma.

Because of their unexpected inhibitory activity against both class I PI3Ks and BRDs, the compounds of the present invention are also useful research tools for studying the mechanism of action of those targets, both in vitro and in vivo, and in immuno-oncology.

An illustration of the preparation of exemplary compounds of the present invention is shown in Schemes below. The specific non-limiting examples of compounds of this invention presented below are intended to illustrate particular embodiments of the present invention, and are not intended to limit the scope of the specification or the claims in any way.

DETAILED DESCRIPTION OF THE INVENTION

Preparation of Exemplary Compounds

The compounds of the present invention may be prepared by the synthetic sequence shown, in Schemes below. A skilled artisan will appreciate that other routes of synthesis may be employed as well. In particular, other routes of synthesis may in fact be applied to certain aspects of the present invention. The skilled artisan is referred to general textbooks, such as March's Advanced Organic Chemistry (Michael B. Smith & Jerry March, Wiley-Interscience, 2000), The Practice of Medicinal Chemistry (Camile G. Wermuth, Academia Press, 2003) and Protective Groups in Organic Synthesis (Theosora W. Greene & Peter G. M. Wuts; John Wiley & Sons Inc, 1999).

Unless otherwise noted, all reagents, starting materials and solvents were obtained from commercial suppliers and used without further purification. Concentration or evaporation refers to evaporation under vacuum using a Buchi rotatory evaporator. Reaction products were purified by silica-gel chromatography with the solvent system indicated, or by HPLC purification using a C18 reverse phase semi-preparative HPLC column with solvent A (0.1% of TFA in water) and solvent B (0.1% of TFA in CH₃CN) as eluents. All final products have at least 95% purity as determined by analytical HPLC analysis with UV detection at 210 nm and/or 254 nm. Reported yields are isolated yields.

Analytical HPLC analysis was performed on an Agilent 1100 HPLC with a phenomenex Luna C18 (2) column (3 micron, 150×4.6 mm id) at a flow rate of 0.6 mL/min, eluting with a binary solvent system A and B using a 5%-70% B in 20 min gradient elution (A: Milli-Q water with 0.1% TFA; B: CH₃CN with 0.1% TFA), NMR spectra were recorded on a Bruker AV-300 300 MHz NMR instrument using DMSO-d₆ or CDCl₃ with TMS as an internal standard. Mass spectra data was obtained with Bruker Esquire Liquid Chromatography-Ion Trap Mass Spectrometer. Chiral HPLC analysis was done with Chiralpak ID-3 or Chiralcel OD-H columns, eluting with isopropanol in hexane.

The following abbreviations are used in the synthetic examples: aq (aqueous), h (hour), min (minutes), sat'd (saturated), THF (tetrahydrofuran), rt (room temperature), Et₃N (triethylamine), n-BuOH (n-butyl alcohol), NaCl (sodium chloride), MgSO₄ (magnesium sulfate), CDCl₃ (deuterated chloroform), H₂O (water), HCl (hydrochloric acid), MeOH (methanol), NaOH (sodium hydroxide), TFA (trifluoroacetic acid), Na₂CO₃ (sodium carbonate). CH₂Cl₂ (methylene chloride), EtOAC (ethyl acetate), DMF (dimethylformamide), EtOH (ethanol), DMSO (dimethyl sulfoxide), DMSO-d₆ (dimethyl sulfoxide-d₅), NaHCO₃ (sodium bicarbonate), HPLC (high performance liquid chromatography), ESI-MS or MS (ESI) (electrospray ionization-mass spectrometry), NMR (nuclear magnetic resonance), DIEA (diisopropylethylamine), brine (saturated aqueous NaCl solution), NH₄Cl (ammonium chloride), BH₃-Me₂S (borane dimethyl sulfide complex), DIAD (diisopropyl azodicarboxylate), DPPA (diphenyl phosphoryl azide), Boc₂O (di-tert-butyl dicarbonate), NaN₃ (sodium azide), NMP (N-Methyl-2-pyrrolidone), Pd(PPh₃)₄ (Tetrakis(triphenylphosphine)palladium(0)), Pd(dppf)₂Cl₂CH₂Cl₂ ([1,1'-Bis(diphenylphosphino)ferrocene]dichloropalladium(II), complex with dichloromethane), Pd₂(dba)₃ (Tris(dibenzylideneacetone)dipalladium(0)), X-Phos (2-Dicyclohexylphosphino-2',4',6'-triisopropylbiphenyl), BrettPhos (2-(Dicyclohexylphosphino)-3,6-dimethoxy-2',4',6'-triisopropyl-1,1'-biphenyl), and other similar standard abbreviations are used herein.

Example 1: Synthesis of 4-amino-6-(2-(6-(3,5-dimethylisoxazol-4-yl)-7-methoxy-2-(piperidin-1-yl)quinolin-3-yl)pyrrolidin-1-yl)pyrimidine-5-carbonitrile (1)

Compound 1 was prepared according to the procedures set forth in steps 1-10 of Scheme 1 below:

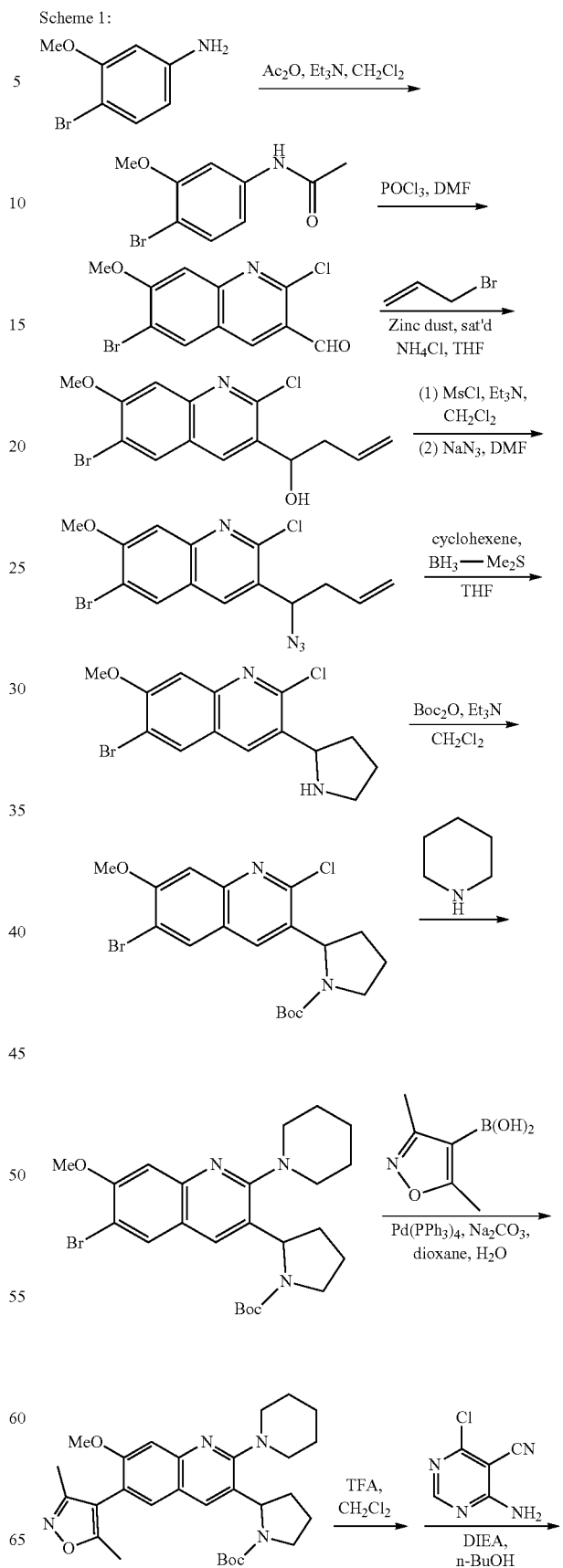

17

-continued

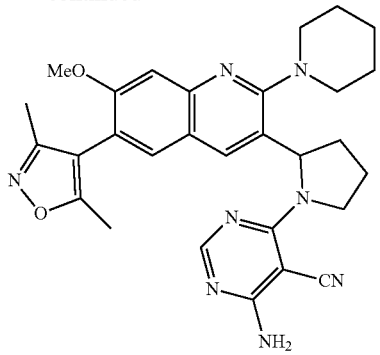

Step 1: N-(4-bromo-3-methoxypheny)acetamide

To a solution of 4-bromo-3-methoxyaniline (2.0 g, 9.9 mmol) ire CH$_2$Cl$_2$ (25 mL) at 0° C. was added Et$_3$N (4.1 mL, 29.7 mmol), followed by dropwise addition of Ac$_2$O (1.4 mL, 14.9 mmol). The reaction mixture was stirred under argon at 0° C. for 0.5 hour and at room temperature overnight, diluted with CH$_2$Cl$_2$ (25 mL) and water (25 mL). The organic layer was further washed with 1 N acetic acid aqueous solution (25 mL), saturated NaHCO$_3$ aqueous solution (25 mL), brine (25 mL), dried (MgSO$_4$). Evaporation to dryness yielded the title product (22 g) as a tan solid. $^1$H NMR (300 MHz, DMSO-d$_6$) δ 2.04 (s, 3H), 3.80 (s, 3H), 7.10 (dd, J=2.0 Hz and 8.6 Hz, 1H), 7.44 (m, 2H), 10.1 (s, 1H).

Step 2: 6-bromo-2-chloro-7-methoxyquinoline-3-carbaldehyde

POCl$_3$ (7.6 mL, 82 mmol) was added dropwise to DMF (2.5 mL, 33 mmol) at 0° C. The resulting mixture was stirred under argon at room temperature for 10 min, and N-(4-bromo-3-methoxyphenyl)acetamide (2.0 g, 82 mmol) was added in one portion. The reaction mixture was stirred at 80° C. overnight, and poured into ice-water after cooling to room temperature. The resulting solid was collected, by filtration and washed with water, saturated NaHCO$_3$ (aq.). Evaporation to dryness gave the title product (2.2 g) as a pale-yellow solid. $^1$H NMR (300 MHz, DMSO-d$_6$) δ 4.07 (s, 3H), 7.59 (s, 1H), 8.64 (s, 1H), 8.88 (s, 1H), 10.3 (s, 1H).

Step 3: 1-(6-bromo-2-chloro-7-methoxyquinolin-3-yl)but-3-en-1-ol

To a solution of 6-bromo-2-chloro-7-methoxyquinoline-3-carbaldehyde (2.2 g, 7.3 mmol) in THF (146 mL) was added zinc dust (2.4 g, 36.7 mmol) and allyl bromide (1.2 mL, 14.2 mmol), followed by dropwise addition of saturated aqueous ammonium chloride solution (73 mL). The reaction mixture was stirred at room temperature for 5 h and filtered via Celite. The filtrate was acidified with 2N HCl (aq.) and extracted with ethyl acetate (100 mL×1, 50 mL×2). The combined organic extracts was washed with brine (50 mL), dried (MgSO$_4$), and concentrated. Purification by silica-gel column chromatography (25% and 50% EtOAc/hexane) yielded the title product (1.7 g) as a white solid. $^1$H NMR (300 MHz, DMSO-d$_6$) δ 2.4 (br m, 2H), 2.6 (br m, 1H), 4.01 (s, 3H), 5.0 (m, 3H), 5.72 (d, J=4.3 Hz, 1H), 5.88 (br m, 1H), 7.48 (s, 1H), 6.44, 8.45 (s, 2H).

Step 4: 3-(1-azidobut-3-enyl)-6-bromo-2-chloro-7-methoxyquinoline

To a solution of 1-(6-bromo-2-chloro-7-methoxyquinolin-3-yl)but-3-en-1-ol (0.81 g, 2.36 mmol) in CH$_2$Cl$_2$ (38 mL) at 0° C. was added Et$_3$N (0.66 mL, 4.8 mmol), followed by slow addition of methanesulfonyl chloride (0.27 mL, 3.5 mmol). The reaction mixture was stirred at 0° C. under argon for one hour and diluted with water (20 mL). The organic layer was further washed with brine (25 mL), dried (Na$_2$SO$_4$). Evaporation under reduced pressure afforded the crude mesylate as a yellow oil, which was immediately used without purification.

To a solution of this mesylate in DMF (16 mL) was added NaN$_3$ (0.23 g, 3.5 mmol). The resulting mixture was stirred at 60° C. for 2.5 hours, diluted with water (50 mL), and, extracted with EtOAc (50 mL×1, 30 mL×2). The combined organic extracts were washed with brine (30 mL×2), dried (MgSO$_4$) and evaporated to dryness. Purification by silica-gel chromatography with 15% EtOAc/hexane gave the azide (0.84 g) as a colorless oil. $^1$H NMR (300 MHz, DMSO-d$_6$) δ 2.73 m, 2H), 4.02 (s, 3H), 5.20-5.25 (m, 3H), 5.82 (br m, 1H), 5.88 (br m, 1H), 7.51 (s, 1H), 8.45, 8.49 (s, 2H).

Step 5: 6-bromo-2-chloro-7-methoxy-3-(pyrrolidin-2-yl)quinoline

To a stirred solution of cyclohexene (1.4 mL, 10.7 mmol) in THF (1.9 mL) at 0° C. was added dropwise 2.0 M BH$_3$-Me$_2$S complex in THF (3.4 mL, 6.8 mmol). The resulting white suspension was stirred for 1 h at 0° C. and then cooled to −15° C. prior to the dropwise addition of 3-(1-azidobut-3-enyl)-6-bromo-2-chloro-7-methoxyquinoline (0.84 g, 2.3 mmol) in THF (6.2 mL). The resulting reaction mixture was allowed to slowly warm to rt. After overnight at rt under argon, the reaction was quenched at 0° C. with MeOH and evaporated to dryness. Purification by silica-gel chromatography with CH$_2$Cl$_2$/MeOH/NH$_4$OH (180:9:1) gave the title compound (0.69 g) as a pale-yellow oily residue. MS (ESI): m/z 341.6, 343.0 (M+H)$^+$; analytical HPLC: 15.7 min (99% pure).

Step 6: tert-butyl 2-(6-bromo-2-chloro-7-methoxyquinolin-3-yl)pyrrolidine-1-carboxylate To a solution of 6-bromo-2-chloro-7-methoxy-3-(pyrrolidin-2-yl)quinoline (0.69 g, 2.0 mmol) in CH$_2$Cl$_2$ (25 mL) was added Boc$_2$O (0.66 g, 3.0 mmol), followed by addition of Et$_3$N (0.41 mL, 3.0 mmol). The reaction mixture was stirred at room temperature under argon overnight, and evaporated to dryness. Purification by silica gel chromatography (25% EtOAc/hexane) yielded the title compound (0.60 g) as a white solid. MS (ESI): m/z 442.0, 443.0 (M+H)$^+$; analytical HPLC: 27.8 min (99% pure).

Step 7: tert-butyl 2-(6-bromo-7-methoxy-2-(piperidin-1-yl)quinolin-3-yl)pyrrolidine-1-carboxylate tert-butyl 2-(6-bromo-2-chloro-7-methoxyquinolin-3-yl)pyrroldine-1-carboxylate (0.2 g, 0.45 mmol) was treated with piperidine (2.0 mL) at 100° C. overnight in a sealed tube. The reaction mixture was cooled to room temperature and evaporated to dryness. Purification by silica-gel chromatography (15% and 25% EtOAc/hexane) afforded the tale product (0.2 g) as a white solid. MS (ESI): m/z 490.9, 491.9 (M+H)$^+$; analytical HPLC: 21.0 min (>99% pure).

Step 8: tert-butyl 2-(6-(3,5-dimethylisoxazol-4-yl)-7-methoxy-2-(piperidin-1-yl)quinolin-3-yl)pyrrolidine-1-carboxylate A mixture of tert-butyl 2-(6-bromo-7-methoxy-2-(piperidin-1-yl)quinolin-3-yl)pyrrolidine-1-carboxylate (89 mg, 0.18 mmol), 3,5-dimethylisoxazol-4-ylboronic acid (38 mg, 0.27 mmol), Pd(PPh$_3$)$_4$ (42 mg, 0.036 mmol), Na$_2$CO$_3$ (58 mg, 0.54 mmol) in dioxane (0.68 mL) and water (0.17 mL) was purged with argon for 5 minutes and then stirred at 100° C. over 20 hours in a sealed tube. The reaction mixture was evaporated to dryness. Purification by chromatography on silica gel (25% EtOAc/hexane) afforded the title product (78 mg) as a white solid. MS (ESI): m/z 507.4 (M+H)$^+$; analytical HPLC: 20.1 min (96% pure).

19

Step 9-10: 4-amino-6-(2-(6-(3,5-dimethylisoxazol-4-yl)-7-methoxy-2-(piperidin-1-yl)quinolin-3-yl)pyrrolidine-1-yl)pyrimidine-5-carbonitrile To a solution tert-butyl 2-(6-(3,5-dimethylisoxazol-4-yl)-7-methoxy-2-(piperidin-1-yl)quinolin-3-yl)pyrrolidine-1-carboxylate (72 mg, 0.14 mmol) in CH$_2$Cl$_2$ (2.5 mL) was added TFA (2.5 mL). The reaction mixture was stirred at room temperature under argon for 1 h. Evaporation and co-evaporation with CHCl$_3$ twice to dryness gave a TFA salt of 4-(7-methoxy-2-(piperidin-1-yl)-3-(pyrrolidin-2-yl)quinolin-6-yl)-3,5-dimethylisoxazole (118 mg) as a pale-yellow oily residue. which was used in the next step without further purification. MS (ESI): m/z 407.3 (M+H)$^+$; analytical HPLC: 14.7 min (>99% pure).

A mixture of 4-(7-methoxy-2-(piperidin-1-yl)-3-(pyrrolidin-2-yl)quinolin-6-yl)-3.5- dimethylisoxazole (TFA salt; 43.6 mg, 0.056 mmol), DIEA (0.030 mL, 0.168 mmol), and 4- amino-6-chloropyrimidine-5-carbonitrile (13 mg, 0.084 mmol) in n-BuOH (0.33 mL) was stirred at 115° C. over 24 hours. The reaction mixture was cooled to room temperature and evaporated to dryness. HPLC purification using a C18 reverse phase semi-preparative HPLC column (H$_2$O+0.1% TFA/CH$_3$CN+0.1% TFA, 95:5 to 25:75 in 40 min) gave the desired product (TFA salt, 31 mg) as a white solid after lyophilization. Further desalting through a Varian Strato-Spheres™ PL-HCO3 MP cartridge and lyophilization afforded the title compound 1 (18 mg) as a white powder. MS (ESI): m/z 525.4 (M+H)$^+$; analytical HPLC: 16.7 min (>99% pure).

Example 2: Synthesis of 4-amino-6-(2-(8-methoxy-1-methyl-7-phenyl-[1,2,4]triazolo[4,3-a]quinolin-4-yl)pyrrolidin-1-yl)pyrimidine-5-carbonitrile (2)

Compound 2 was prepared according to the procedures set forth in steps 1-4 of Scheme 2 below:

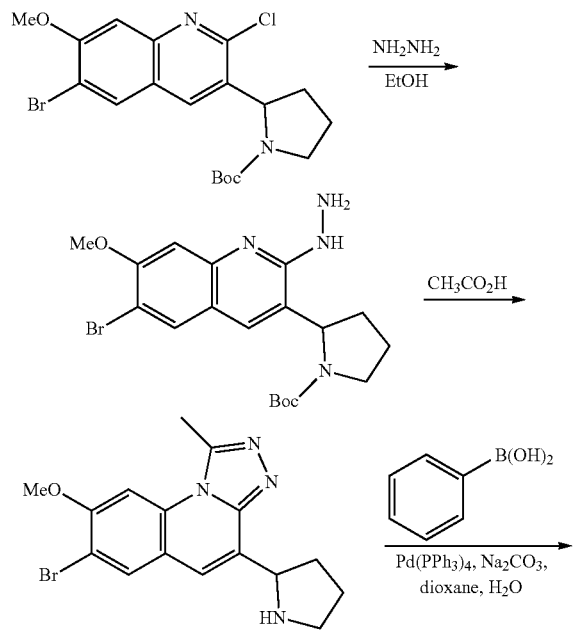

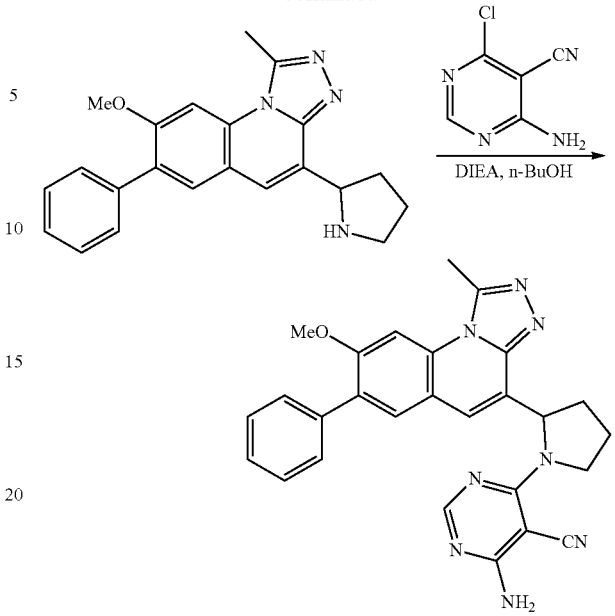

Step 1: tert-butyl 2-(6-bromo-2-hydrazinyl-7-methoxyquinolin-3-yl)pyrrolidine-1-carboxylate tert-butyl 2-(6-bromo-2-chloro-7-methoxyquinolin-3-yl)pyrrolidine-1-carboxylate (120 mg, 0.27 mmol) was treated with hydrazine monohydrate (1.0 mL) in EtOH (1 mL) at 110° C. over 24 hours in a sealed tube. The reaction mixture was cooled to room temperature and evaporated to dryness afforded the title compound as a yellow solid. MS (ESI): m/z 437.5, 439.0 (M+H)$^+$; analytical HPLC: 18.8 min.

Step 2: 7-bromo-8-methoxy-1-methyl-4-(pyrrolidin-2yl)-[1,2,4]triazolo[4,3-a]quinoline tert-butyl 2-(6-bromo-2-hydrazinyl-7-methoxyquinolin-3-yl)pyrrolidine-1-carboxylate (75 mg, 0.19 mmol) in acetic acid (3 mL) was stirred at 100° C. for 3 hours. Evaporation to dryness and purification by silica-gel chromatography with CH$_2$Cl$_2$/MeOH/NH$_4$OH (180:9:1, and 90:9:1) gave the desired compound (50 mg) as an orange residue. MS (ESI): m/z 361.5, 362.8 (M+H)$^+$; analytical HPLC: 14.8 min.

Step 3: 8-methoxy-1-methyl-7-phenyl-4-(pyrrolidin-2-yl)-[1,2,4]triazolo[4,3-a]quinoline A mixture of 7-bromo-8-methoxy-1-methyl-4-(pyrrolidin-2-yl)-[1,2,4]triazolo[4,3-a]quinoline (50 mg, 0.11 mmol), phenylboronic acid (19.3 mg, 0.16 mmol), Pd(PPh$_3$)$_4$ (24 mg), Na$_2$CO$_3$ (34 mg) in dioxane (0.4 mL) and water (0.1 mL) was purged with argon for 5 minutes and then stirred at 100° C. over 20 hours in a sealed tube. The reaction mixture was evaporated to dryness. Purification by silica-gel chromatography with CH$_2$Cl$_2$/MeOH/NH$_4$OH (180:9:1, and 90:9:1) gave the desired compound (23 mg) as a yellow residue. MS (ESI): m/z 359.3 (M+H)$^+$; analytical HPLC: 16.9 min.

Step 4: 4-amino-6-(2-(8-methoxy-1-methyl-7-phenyl-[1,2,4]triazolo[4,3-a]quinolin-4-yl)pyrrolidin-1-yl)pyrimidine-5-carbonitrile A mixture of 8-methoxy-1-methyl-7-phenyl-4-(pyrrolidin-2-yl)-[1,2,4]triazolo[4,3-a]quinoline (23 mg, 0.064 mmol), DIEA (0.027 mL, 0.15 mmol), and 4-amino-6-chloropyrimidine-5-carbonitrile (11.7 mg, 0.076 mmol) in n-BuOH (0.3 mL) was stirred at 115° C. over 22 hours in a sealed tube. The reaction mixture was cooled to room temperature and evaporated to dryness. HPLC purification using a C18 reverse phase semi-preparative HPLC column (H₂O+0.1% TFA/CH₃CN+0.1% TFA, 95:5 to 25:75 in 40 min) gave the title product (TFA salt, 30 mg) as a faint yellow solid after lyophilization. Further desalting through a Varian StratoSpheres™ PL-HCO3 MP cartridge afforded the title compound 2 (25 mg) as a white powder. MS (ESI): m/z 477.3 (M+H)⁺; analytical HPLC: 18.3 min (>99% pure).

Example 3: Synthesis of 4-amino-6-(2-(2-(3,5-dimethylisoxazol-4-yl)-8-methylquinolin-3-yl)pyrrolidin-1-yl)pyrimidine-5-carbonitrile (3)

Compound 3 was prepared according to the procedures set forth in steps 1-3 of Scheme 3 below:

Step 2-3: 4-amino-6-(2-(2-(3,5-dimethylisoxazol-4-yl-8-methylquinolin-3-yl)pyrrolidin-1-yl)pyrimidine-5-carbonitrile The title compound 3 was obtained, according to the procedures described in Step 9-10 of Example 1. MS (ESI): m/z 426.4 (M+H)⁺; analytical HPLC: 19.1 min (>99% pure).

Example 4: Synthesis of 4-amino-6-(2-(7-fluoro-2-(4-(3-methyl-[1,2,4]triazolo[4,3-b]pyridazin-6-yl)piperazin-1-yl)quinolin-3-yl)pyrrolidin-1-yl)pyrimidine-5-carbonitrile (4)

Compound 4 was prepared according to the procedures set forth in steps 1-5 of Scheme 4 below:

Scheme 3:

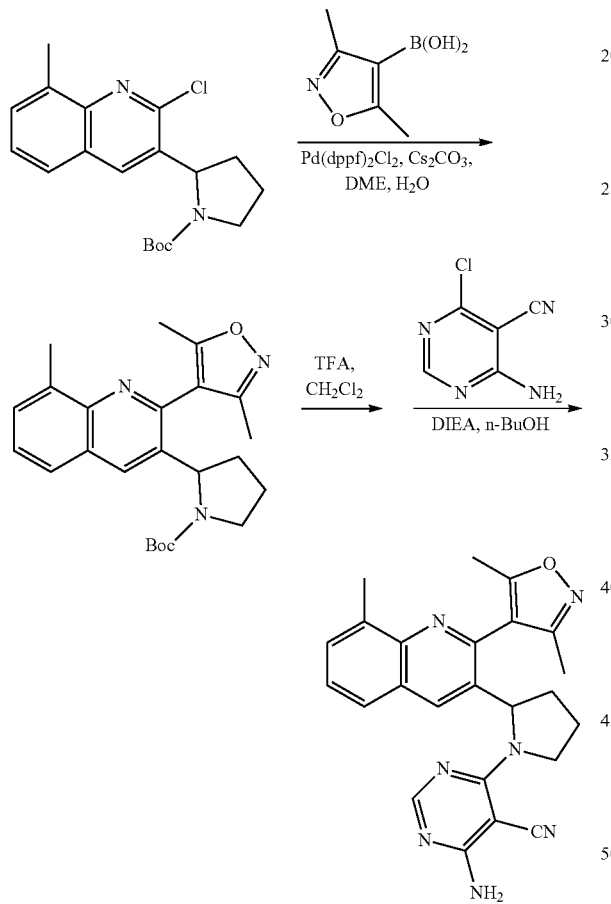

Scheme 4:

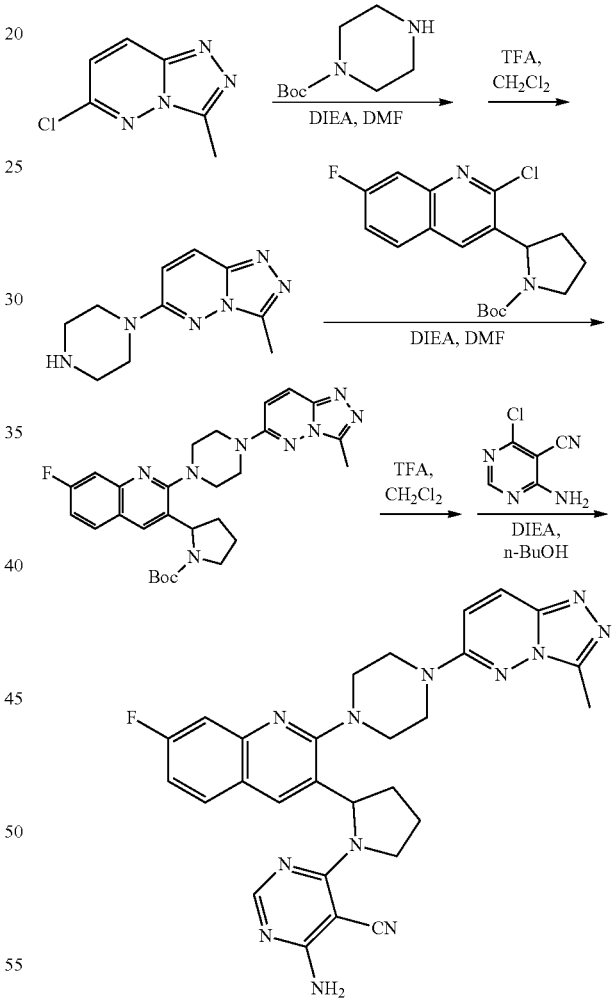

Step 1: tert-butyl 2-(2-(3,5-dimethylisoxazol-4-yl)-8-methylquinolin-3-yl)pyrrolidine-1-carboxylate A mixture of tert-butyl 2-(2-chloro-8-methylquinolin-3-yl)pyrrolidine-1-carboxylate (30 mg, 0.087 mmol; that was prepared according to the procedures disclosed in U.S. Pat. No. 9,637,488, 3,5-dimethylisoxazol-4-ylboronic acid (13.7 mg, 0.097 mmol), and Pd(dppf)₂Cl₂CH₂Cl₂ (3.5 mg), Cs₂CO₃ (100 mg) in water (0.27 mL) and 1,2-domethoxyethane (0.81 mL) was purged with argon for 5 min and then stirred at 90° C. overnight in a sealed tube. The reaction mixture was cooled to room temperature, and evaporated to dryness. Purification by silica gel chromatography using EtOAc/hexane (12.5% to 25%) afforded the title compound (6.8 mg) as a white solid. MS (ESI): m/z 480.4 (M+H)⁺.

Step 1-2: 3-methyl-6-(piperazin-1-yl)-[1,2,4]triazolo[4,3-b]pyridazine

A reaction mixture of 6-chloro-3-methyl-[1,2,4]triazolo[4,3-b]pyridazine (0.40 g, 2.37 mmol), tert-butyl piperazine-1-carboxylate (0.49 g, 2.6 mmol), and DIEA (0.77 mL, 4.4 mmol) in DMF (5 mL) was stirred at 80 overnight in a sealed tube. The reaction mixture was cooled to room temperature, and poured into water. The precipitation was collected by filtration, followed by extensive washing with water. Dryness via high vacuum afforded tert butyl 4-(3-methyl-[1,2, 4]triazolo[4,3-b]pyridazin-6-yl)piperazine-1-carboxylate (0.55 g) as a yellow solid.

To a solution of tert-butyl 4-(3-methyl-[1,2,4]triazolo[4, 3-b]pyridazin-6-yl)piperazine-1-carboxylate (0.10 g, 0.32 mmol) in $CH_2Cl_2$ (2 mL) was added TFA (2 mL). The reaction mixture was stirred at room temperature under argon for 1 h. Evaporation and co-evaporation with $CHCl_3$ twice to dryness gave the title compound (TFA salts) as dark brownish residue, which was used in the next step without further purification. MS (ESI): m/z 219.3 $(M+H)^+$; analytical HPLC: 7.7 min.

silica-gel chromatography (10% $MeOH/CH_2Cl_2$) afforded the title product (17 mg) as a brown oil. MS (ESI): m/z 533.5 $(M+H)^+$; analytical HPLC: 19.5 min.

Step 4-5: 4-arnino-6-(2-(7-fluoro-2-(4-(3-methyl-[1,2,4]triazolo[4,3-b]pyridazin-6-yl)piperazin-1-yl)quinolin-3-yl) pyrrolidin-1-yl)pyrimidine-5-carbonitrile The title compound 4 was obtained, according to the procedures described in Step 9-10 of Example 1. MS (ESI): m/z 551.5 $(M+H)^+$; analytical HPLC: 18.5 min (>99% pure).

Example 5: Compounds 5-26 listed in Table 1 were prepared according to Scheme 5, using procedures analogs to that used in Example 1-4.

Scheme 5:

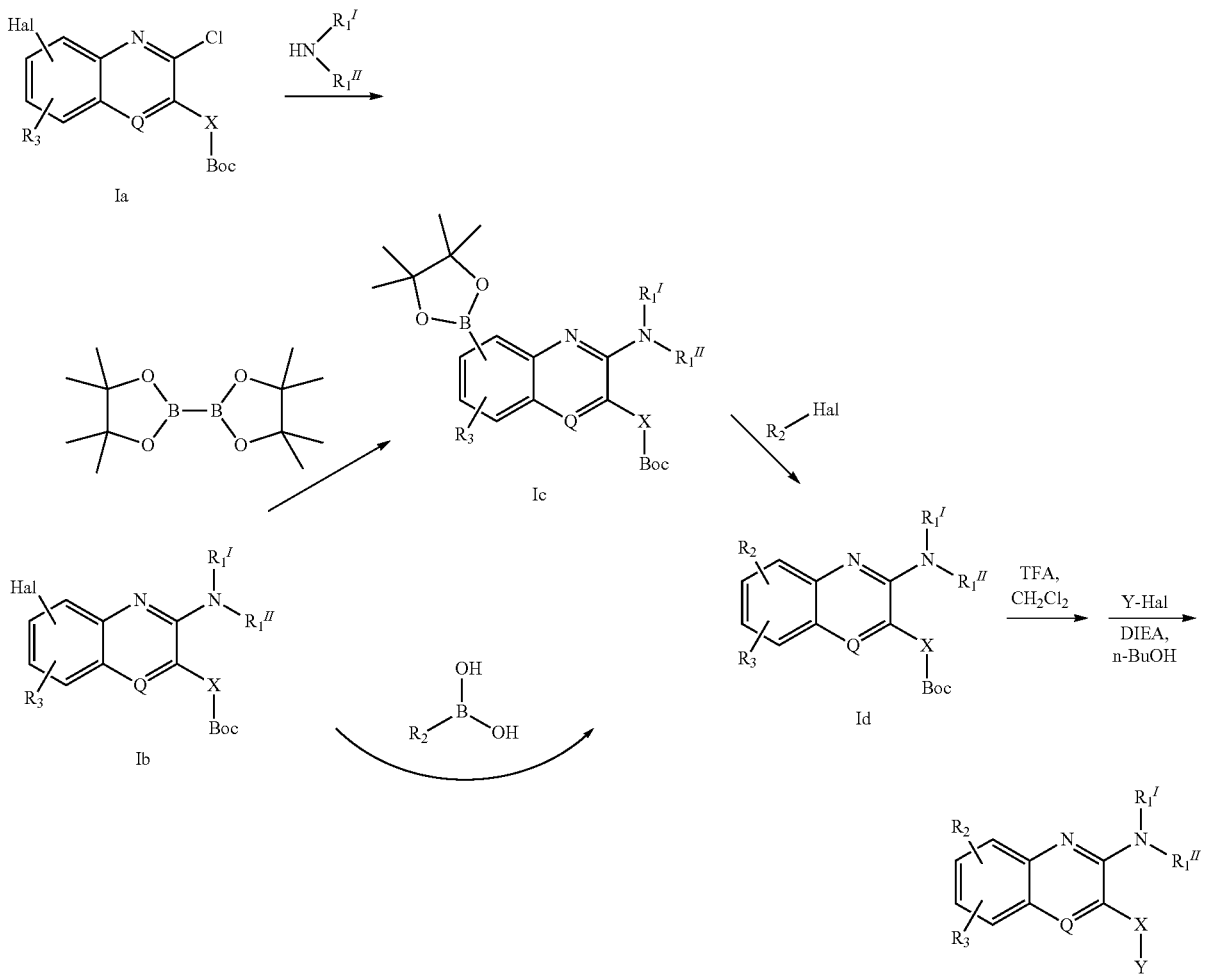

Step 3: tert-butyl 2-(7-fluoro-2-(4-(3-methyl-[1,2,4]triazolo [4,3-b]pyridazin-6-yl)piperazin-1-yl)quinolin-3-yl)pyrrolidine-1-carboxylate A reaction mixture tert-butyl 2-(2-chloro-7-fluoroquinolin-3-yl)pyrrolidine-1-carboxylate (80 mg, 0.23 mmol; that was prepared according to the procedures disclosed in U.S. Pat. No. 9,637,488, 3-methyl-6-(piperazin-1-yl)-[1,2,4]triazolo[4,3-b]pyridazine (0.32 mmol), DIEA (0.28 mL, 1.6 mmol) in DMF(1.5 mL) was stirred at 100° C. over 24 hours in a sealed tube. The reaction mixture was cooled to room temperature and evaporated to dryness. Purification by Hal is a halogen, such as a bromide or a chloride; $R_3$ is a hydrogen or a deuterium or a fluorine; $R_1^I$ and $R_1^{II}$ are selected from a hydrogen, small alkyl, and/or $R_1^I$ and $R_1^{II}$ are taken, together to form $C_3$-$C_7$ cycloalkyl or $C_4$-$C_7$ heterocycloalkyl; $R_2$, X, Y, Q are as defined above for a compound of the invention.

Step 1: Synthesis of Ib from Ia

Intermediate Ia was treated with large excess amount of the corresponding amine ($NHR_1^{II}R_1^{II}$) in neat form or in THF or DMF at elevated temperature (e.g., 100° C.) for 12 hours to 48 hours in a sealed tube. The reaction mixture was cooled to room temperature and evaporated to dryness. Purification by silica-gel chromatography afforded Ib.

Step 2: Synthesis Id, from Ib

Intermediate Id was obtained from Ib through Pd-mediated cross coupling reactions: (1) R$_2$-B(OH)$_2$, Pd(OAc)$_2$, BrettPhos, Na$_2$CO$_3$ in NMP under argon atmosphere at elevated temperature (e.g., 160° C.) for days (see: e.g., a procedure disclosed in WO 2015/010641); or (2) R$_2$-Hal, Ic, Pd(PPh$_3$)$_4$, Na$_2$CO$_3$, H$_2$O, dioxane or DMF under argon atmosphere at elevated temperature for at least, overnight. Ic was obtained by treating Ib with bis(pinacolato)diboron, Pd(dppf)$_2$Cl$_2$CH$_2$Cl$_2$, KOAc in dioxane under argon atmosphere at 100° C. for 3 hours (see: e.g., Martin, L. J., et al., J Med Chem. 2016; 59:4462-4475), Purification of Id was carried out by silica-gel chromatography or preparative HPLC.

Step 4-5: Compounds 5-26 listed in Table 1 from Id

Deprotection of Id with TFA in CH$_2$Cl$_2$ at room temperature, followed by reacting with Y-Hal in DIEA and n-BuOH at 115° C. gave the desired product. In the case of protected R$_2$-Hal, final products were obtained after treatment with KOH in MeOH at 65° C. for hours (see: e.g., Crawford, T. D., et al., J Med Chem. 2016; 59:5391-5402). All final products were purified by preparative TLC, or preparative HPLC and followed by desalting through a Varian Strato-Spheres™ PL-HCO3 MP cartridge.

TABLE 1

| Compound | Structure | Analytical HPLC Tr (min)/purity | MS (ESI) [m/z (M + H)$^+$] |
|---|---|---|---|
| 5 | | 16.7/99% | 497.4 |
| 6 | | 15.1/98% | 548.5 |
| 7 | | 16.7/98% | 534.5 |

TABLE 1-continued
| Compound Structure | Analytical HPLC Tr (min)/purity | MS (ESI) [m/z (M + H)⁺] |
|---|---|---|
| 8 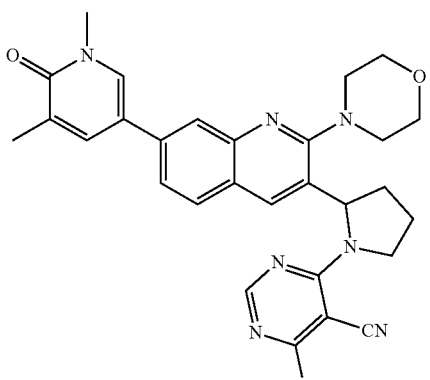 | 13.8/98% | 523.4 |
| 9 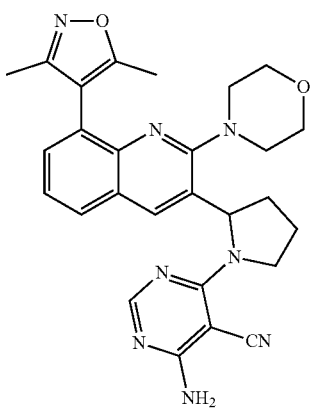 [SMILES: Cc1noc(C)c1-c1cccc2cc(C3CCCN3c3ncnc(N)c3C#N)c(N3CCOCC3)nc12] | 19.6/>95% | 497.4 |
| 10 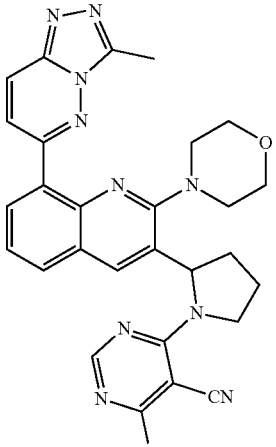 | 18.3/98% | 534.2 |

TABLE 1-continued
| Compound Structure | Analytical HPLC Tr (min)/purity | MS (ESI) [m/z (M + H)+] |
|---|---|---|
| 11 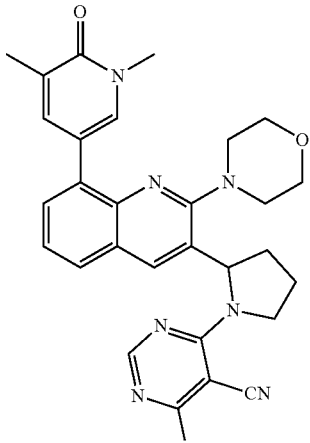 | 18.2/99% | 523.4 |
| 12 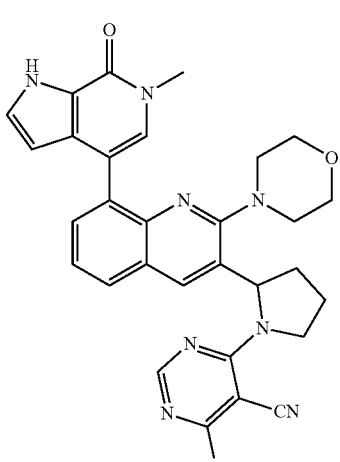 | 18.0/90% | 548.2 |
| 13 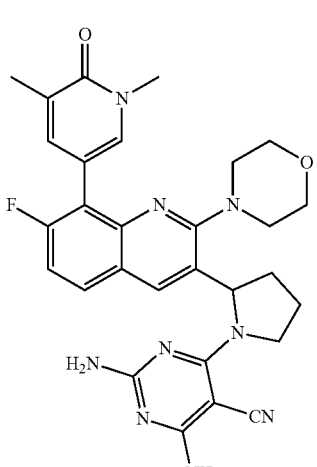 | 15.0/98% | 556.4 |

TABLE 1-continued
| Compound Structure | Analytical HPLC Tr (min)/purity | MS (ESI) [m/z (M + H)+] |
|---|---|---|
| 14 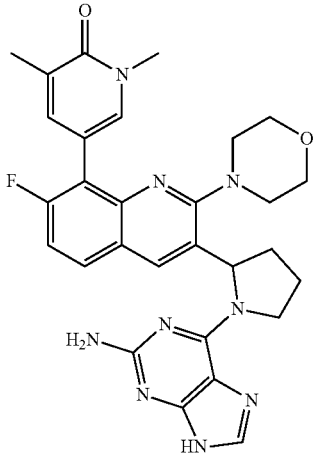 [SMILES: Cc1cc(-c2c(F)ccc3cc(C4CCCN4c4nc(N)nc5[nH]cnc45)c(N4CCOCC4)nc23)cn(C)c1=O] | 14.1/99% | 556.9 |
| 15 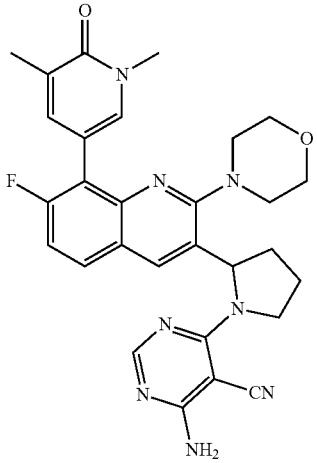 [SMILES: Cc1cc(-c2c(F)ccc3cc(C4CCCN4c4ncnc(N)c4C#N)c(N4CCOCC4)nc23)cn(C)c1=O] | 15.4/99% | 541.4 |
| 16 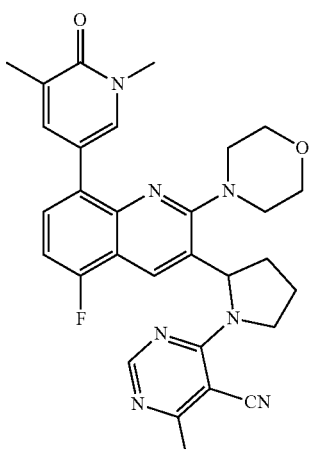 | 17.0/98% | 541.4 |

TABLE 1-continued
| Compound Structure | Analytical HPLC Tr (min)/purity | MS (ESI) [m/z (M + H)+] |
|---|---|---|
| 17 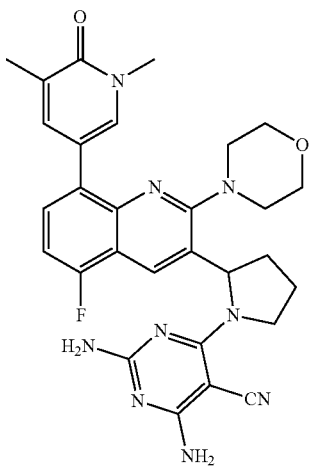 [SMILES: Cc1cc(-c2ccc(F)c3cc(C4CCCN4c4nc(N)nc(N)c4C#N)c(N4CCOCC4)nc23)cn(C)c1=O] | 16.5/100% | 556.4 |
| 18 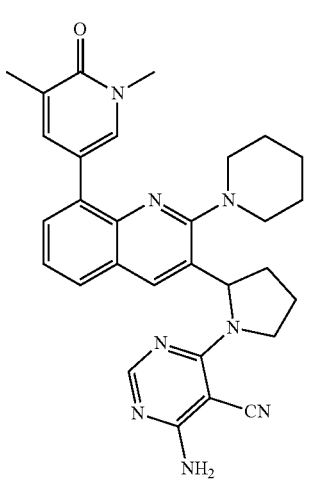 [SMILES: Cc1cc(-c2cccc3cc(C4CCCN4c4ncnc(N)c4C#N)c(N4CCCCC4)nc23)cn(C)c1=O] | 18.1/92% | 521.5 |
| 19 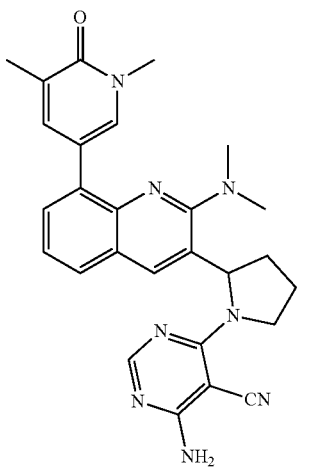 [SMILES: Cc1cc(-c2cccc3cc(C4CCCN4c4ncnc(N)c4C#N)c(N(C)C)nc23)cn(C)c1=O] | 14.4/100% | 481.4 |

TABLE 1-continued
| Compound Structure | Analytical HPLC Tr (min)/purity | MS (ESI) [m/z (M + H)+] |
|---|---|---|
| 20 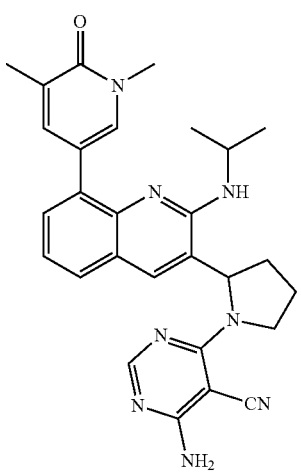 [SMILES: Cc1cc(-c2cccc3cc(C4CCCN4c4ncnc(N)c4C#N)c(NC(C)C)nc23)cn(C)c1=O] | 13.3/97% | 510.5 |
| 21 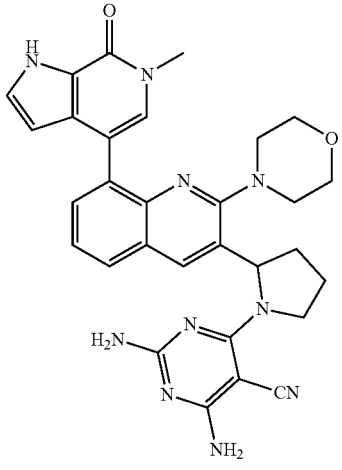 | 16.2/99% | 563.5 |
| 22 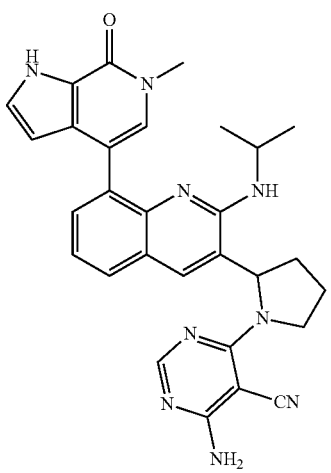 [SMILES: CC(C)Nc1nc2c(-c3cn(C)c(=O)c4[nH]ccc34)cccc2cc1C1CCCN1c1ncnc(N)c1C#N] | 13.7/99% | 520.5 |

TABLE 1-continued
| Compound Structure | Analytical HPLC Tr (min)/purity | MS (ESI) [m/z (M + H)+] |
|---|---|---|
| 23 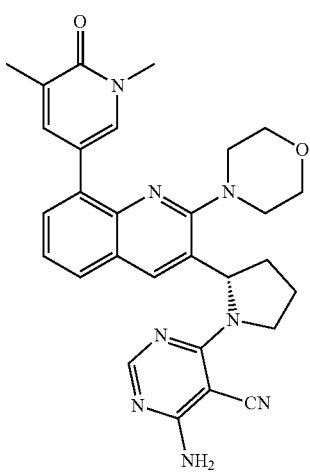 [SMILES: Cc1cc(-c2cccc3cc([C@@H]4CCCN4c4ncnc(N)c4C#N)c(N4CCOCC4)nc23)cn(C)c1=O] | 17.3/95% | 523.5 |
| 24 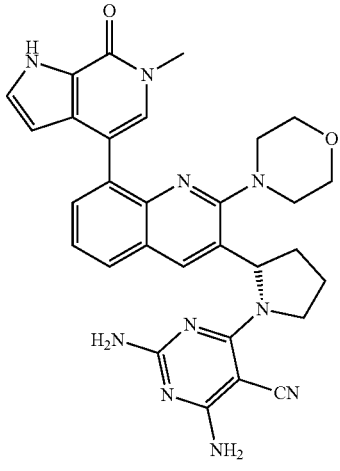 | 16.2/99% | 563.5 |
| 25 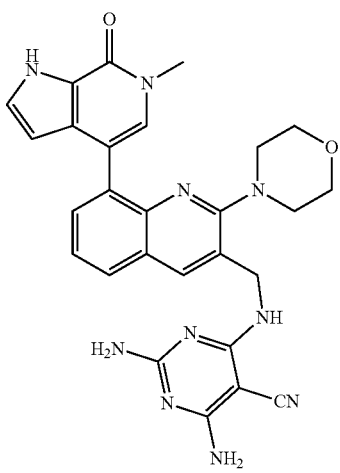 [SMILES: Cn1cc(-c2cccc3cc(CNc4nc(N)nc(N)c4C#N)c(N4CCOCC4)nc23)c2cc[nH]c2c1=O] | 13.8/99% | 523.3 |

TABLE 1-continued

| Compound Structure | Analytical HPLC Tr (min)/purity | MS (ESI) [m/z (M + H)+] |
|---|---|---|
| 26 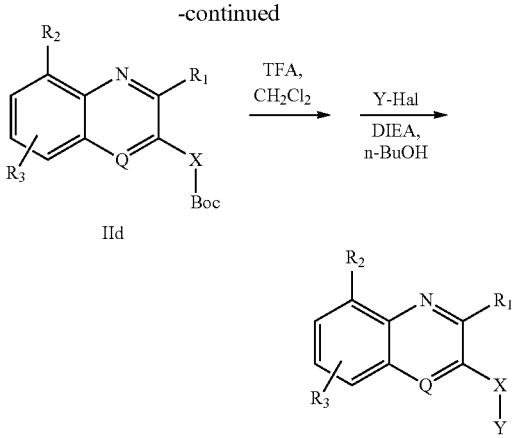 | 17.0/99% | 538.3 |

Example 6: Exemplary compounds listed in Table 2 were prepared according to Scheme 6, using procedures analogs to that, used in Example 1-4.

Scheme 6:

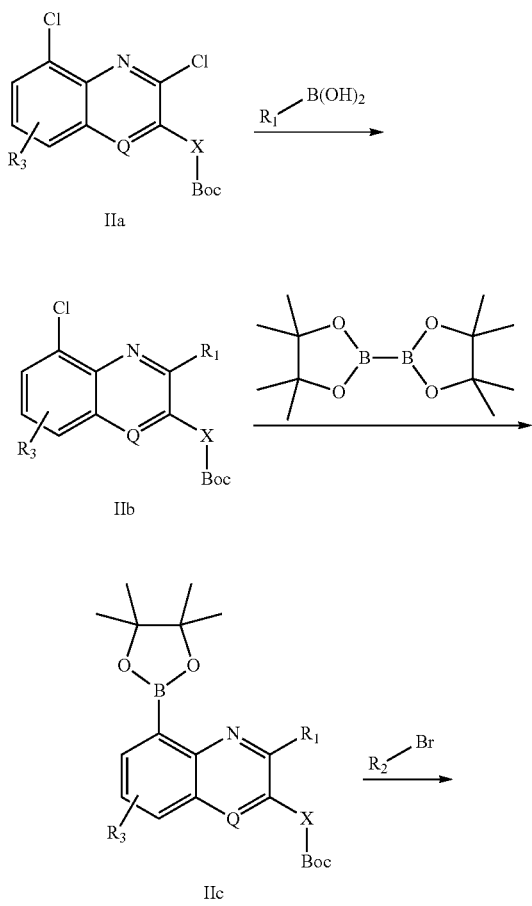

Hal is a halogen, such as a bromide or a chloride; $R_3$ is a hydrogen or a deuterium; $R_1$ is selected from a aryl, heteroaryl, cycloalkyl, or heterocycloalkyl; $R_2$, X, Y, Q are as defined above for a compound of the invention.

Step 1: Synthesis of IIb from IIa

Intermediate IIb was obtained by reacting IIa with $R_1$-B$(OH)_2$, Pd(PPh$_3$)$_4$, Na$_2$CO$_3$ in CH$_3$CN and water under argon atmosphere at elevated temperature (e.g., 90° C.) for hours in a sealed tube. The reaction mixture was cooled to room temperature and evaporated to dryness. Purification by silica-gel chromatography afforded IIb (see: procedure disclosed in U.S. Pat. No. 9,637,488)

Step 2: Synthesis IIc from IIb

Intermediate IIe was obtained by treating IIb with bis(pinacolato)diboron, Pd$_2$(dba)$_3$, X-Phos, KOAc in dioxane under argon atmosphere at 100° C. over 16 hours (see: Yu, W., et al., J Med Chem. 2018; 61:3984-4003).

Step 3: Synthesis IId from IIc $R_2$-Hal, IIc, Pd(PPh$_3$)$_4$, Na$_2$CO$_3$, H$_2$O, dioxane or DMF under argon atmosphere at elevated temperature for at least overnight (see: e.g., Martin, L. J, et al., J Med Chem. 2016; 59:4462-4475). Purification of IId was carried out by silica-gel chromatography or preparative HPLC.

Step 4-5: Exemplary compounds listed in Table 2

Deprotection of IId with TFA in CH$_2$Cl$_2$ at room temperature, followed by reacting with Y-Hal in DIEA and n-BuOH at 115° C. gave the desired product. In the case of protected R$_2$-Hal, final products were obtained after treatment with KOH in MeOH at 65° C. for hours (see: e.g., Crawford, T. D., et al., J Med Chem. 2016; 59:5391-5402). All final products were purified by preparative TLC, or preparative HPLC and followed by desalting through a Varian StratoSpheres™ PL-HCO3 MP cartridge.

TABLE 2

| Compound Structure | Analytical HPLC Tr (min)/purity | MS (ESI) [m/z (M + H)$^+$] |
|---|---|---|
| 27 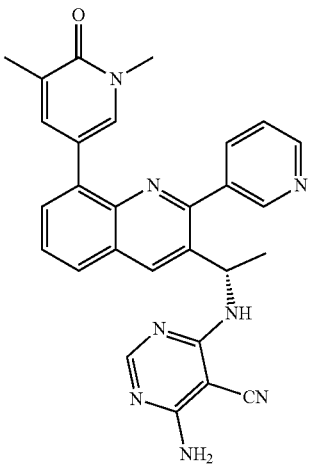 [SMILES: Cc1cc(-c2cccc3cc([C@H](C)Nc4ncnc(N)c4C#N)c(-c4cccnc4)nc23)cn(C)c1=O] | 17.7/99% | 506.4 |
| 28 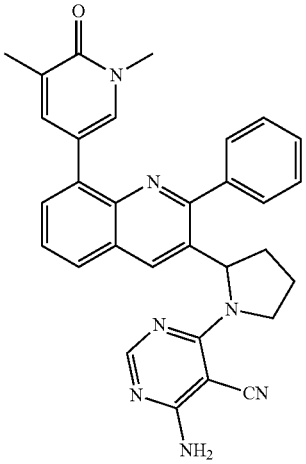 [SMILES: Cc1cc(-c2cccc3cc(C4CCCN4c4ncnc(N)c4C#N)c(-c4ccccc4)nc23)cn(C)c1=O] | 18.2/100% | 514.5 |
| 29 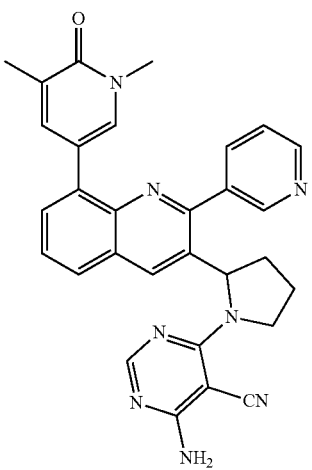 [SMILES: Cc1cc(-c2cccc3cc(C4CCCN4c4ncnc(N)c4C#N)c(-c4cccnc4)nc23)cn(C)c1=O] | 13.9/95% | 515.4 |

TABLE 2-continued

| Compound Structure | Analytical HPLC Tr (min)/purity | MS (ESI) [m/z (M + H)+] |
|---|---|---|
| 30 [structure] | 13.3/97% | 489.3 |

Example 9: Intermediates and starting materials used for the preparation of exemplary compounds were listed in Table 3.

TABLE 3

| Intermediates and Starting Materials | Structure | CAS # or comment on synthesis |
|---|---|---|
| Ia | [structure: 7-Br, 2-Cl quinoline with 3-(N-Boc-pyrrolidin-2-yl)] | Prepared according to the procedures described above in Example 1 or disclosed in U.S. Pat. No. 9,637,488, starting from N-(3-bromophenyl)acetamide |
| Ia | [structure: 8-Br, 2-Cl quinoline with 3-(N-Boc-pyrrolidin-2-yl)] | Prepared according to the procedures described above in Example 1 or disclosed in U.S. Pat. No. 9,637,488, starting from 8-bromo-2-chloroquinoline-3-carbaldehyde |
| Ia | [structure: 8-Br, 7-F, 2-Cl quinoline with 3-(N-Boc-pyrrolidin-2-yl)] | Prepared according to the procedures described above in Example 1 and disclosed in U.S. Pat. No. 9,637,488, starting from 8-bromo-2-chloro-7-fluoroquinoline-3-carbaldehyde that was prepared based on the procedures described in Example 8 |
| Ia | [structure: 8-Br, 5-F, 2-Cl quinoline with 3-(N-Boc-pyrrolidin-2-yl)] | Prepared according to the procedures described above in Example 1 and disclosed in U.S Pat. No. 9,637,488, starting from 8-bromo-2-chloro-5-fluoroquinoline-3-carbaldehyde that was prepared based on the procedures described in Example 9 |

TABLE 3-continued

| Intermediates and Starting Materials | Structure | CAS # or comment on synthesis |
|---|---|---|
| Ia | 8-bromo-2-chloro-3-(N-Boc-pyrrolidin-2-yl)quinoline | Prepared according to the procedures disclosed in U.S. Pat. No. 9,637,488, starting from 8-bromo-2-chloroquinoline-3-carbaldehyde |
| Ia | 8-bromo-2-chloro-3-(NHBoc-methyl)quinoline | Prepared according to the procedures disclosed in WO 2008/118468, starting from 8-bromo-2-chloroquinoline-3-carbaldehyde |
| Ia | 8-bromo-2-chloro-3-(1-NHBoc-ethyl)quinoline | Prepared according to the procedures disclosed in WO 2008/118468, starting from 8-bromo-2-chloroquinoline-3-carbaldehyde |
| IIa | 2,8-dichloro-3-(1-NHBoc-ethyl)quinoline | Prepared according to the procedures disclosed in WO 2008/118468, starting from 2,8-dichloroquinoline-3-carbaldehyde |
| IIa | 2,8-dichloro-3-(N-Boc-pyrrolidin-2-yl)quinoline | Prepared according to the procedures disclosed in U.S. Pat. No. 9,637,488, starting from 2,8-dichloroquinoline-3-carbaldehyde |
| $R_2$ precursor | 5-bromo-1,6-dimethylpyridin-2(1H)-one | 51417-13-1 |
| $R_2$ precursor (protected) | 4-bromo-6-methyl-1-tosyl-1H-pyrrolo[2,3-c]pyridin-7(6H)-one | 1445993-87-2 |

TABLE 3-continued

| Intermediates and Starting Materials | Structure | CAS # or comment on synthesis |
|---|---|---|
| R₂ precursor | 3,5-dimethylisoxazole-4-boronic acid | 16114-47-9 |
| R₂ precursor | 6-chloro-3-methyl-[1,2,4]triazolo[4,3-b]pyridazine | 7197-01-5 |
| R₁ precursor [R₁ᴵ—NH—R₁ᴵᴵ] | morpholine | 110-89-4 |
| R₁ precursor [R₁ᴵ—NH—R₁ᴵᴵ] | piperidine | 110-89-4 |
| R₁ precursor [R₁ᴵ—NH—R₁ᴵᴵ] | dimethylamine | 124-40-3 |
| R₁ precursor [R₁ᴵ—NH—R₁ᴵᴵ] | isopropylamine | 75-31-0 |
| R₁ precursor [R₁—B(OH)₂] | phenylboronic acid | 98-80-6 |
| R₁ precursor [R₁—B(OH)₂] | 3-fluorophenylboronic acid | 768-35-4 |
| R₁ precursor [R₁—B(OH)₂] | pyridine-3-boronic acid | 1692-25-7 |
| Y precursor | 6-amino-4-chloropyrimidine-5-carbonitrile | 60025-09-04 |
| Y precursor | 2,6-diamino-4-chloropyrimidine-5-carbonitrile | Prepared according to the procedure disclosed in Example 3 of WO 2014/201409 |

TABLE 3-continued

| Intermediates and Starting Materials | Structure | CAS # or comment on synthesis |
|---|---|---|
| Y precursor | (structure: 2-amino-6-chloropurine) | 10310-21-1 |

Example 9: Synthesis or 8-bromo-2-chloro-7-fluoroquinoline-3-carbaldehyde 8-bromo-2-chloro-7-fluoroquinoline-3-carbaldehyde was prepared according to the procedures set forth in steps 1-4 of Scheme 7 below:

Scheme 7:

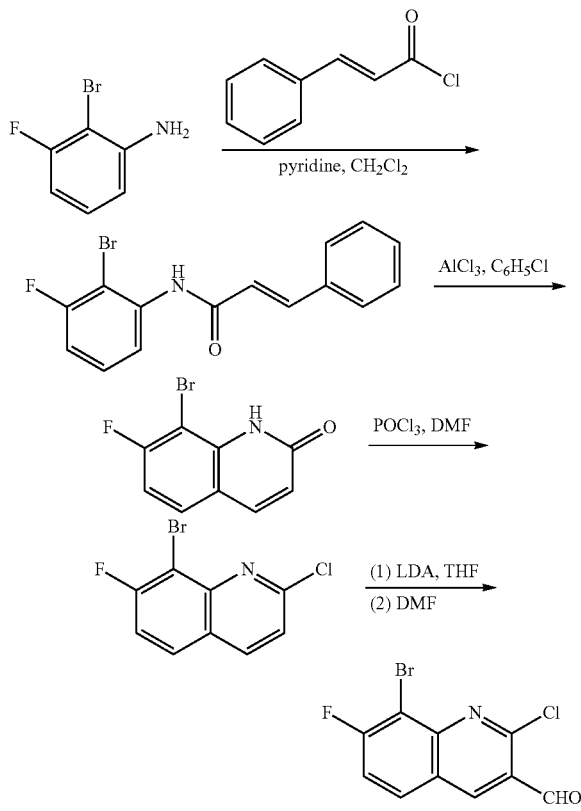

Step 1: N-(2-bromo-3-fluorophenyl)cinnarnamide

To a solution of 2-bromo-3-fluoroanilinne (2.5 g, 13.2 mmol) and pyridine (1.1 mL, 13.2 mmol) in $CH_2Cl_2$ (8 mL) was added dropwise a solution of cinnamoyl chloride (2.3 g, 13.7 mmol) in $CH_2Cl_2$ (4 mL). The reaction mixture was stirred at room temperature under argon overnight, diluted with CH2Cl2 and evaporated to dryness. Purification by silica gel chromatography using EtOAc (100 mL). The solution was washed with 1 N HCl (50 mL), sated $NaHCO_3$ (50 mL), brine (50 mL) and dried ($NaSO_4$). Evaporation in vacua afforded the title compound (4.3 g) as a white so-lid. $^1$H NMR (300 MHz, $CDCl_3$) δ 6.60 (d, J=15.3 Hz, 1H), 6.92 (t, J=8.1 Hz, 1H), 7.26-7.42 (m, 4H), 7.58 (m, 2H), 7.80 (d, J=15.6 Hz, 2H), 8.36 (d, J=8.4 Hz, 1H), Step 2: 8-bromo-7-fluoroquinolin-2(1H)-one To a mixture of N-(2-bromo-3-fluorophenyl)cinnamamide (2.2 g, 6.9 mmol) in chlorobebzene (15 mL) was added $AlCl_3$ (3.5 g, 33.7 mmol) portionwise. The reaction mixture was stirred at 130° C. for 2 hours, poured into ice water and filtered, and the solid was extracted with $CH_2Cl_2$. The filtrate was dried ($Na_2SO_4$), concentrated and purified by silica gel chromatography using 2.5% MeOH/$CH_2Cl_2$ to give the title compound (1.2 g) as a purple solid. $^1$H NMR (300 MHz, $CDCl_3$) δ 6.62 (d, J=9.7 Hz, 1H), 7.03 (t, J=8.4 Hz, 1H), 7.52 (dd, J=5.5 Hz and 8.7 Hz, 1H), 7.70 (d, J=9.6 Hz, 1H), 9.01 (br s, 1H).

Step 3: 8-bromo-2-chloro-7-fluoroquinoline

A mixture of 8-bromo-7-fluoroquinolin-2(1H)-one (12 g, 5.0 mmol) in $POCl_3$ (6 mL) was stirred at 110° C. for 2 hours, poured into ice water. The solid was collected by filtration, washed with water, sat'd $NaCO_3$ and water, and dried in vacuo to give the title compound (1.2 g) as a pink solid. $^1$H NMR (300 MHz, $CDCl_3$) δ 7.43 (m, 2H), 7.80 (m, 1H), 8.12 (d, J=8.7 Hz, 1H).

Step 4: 8-bromo-2-chloro-7-fluoroquinoline-3-carbaldehyde

To a solution of LDA (3.3 mL, 1.5 M) in THF (3.7 mL) at −78° C. under argon was added dropwise a solution of 8-bromo-2-chloro-7-fluoroquinoline (1.18 g, 45.3 mmol) in THF (10 mL). After 0.5 hour, DMF (0.18 mL) was added. The reaction mixture was stirred at −78° C. for 0.5 hour, quenched by sated $NH_4Cl$ (aq.) and taken into EtOAc and water. The aqueous layer was further extracted with EtOAc. The combined organic extracts were washed with water, sat'd $Na_2CO_3$, and dried ($Na_2SO_4$). Purification by silica. gel chromatography using 25% EtOAc/Hexane gave the title compound (0.74 g) as a brown solid. $^1$H NMR (300 MHz, $CDCl_3$) δ 7.52 (d, J=8.4 Hz, 1H), 8.25 (d, J=8.6 Hz, 1H), 8.39 (d, J=7.0 Hz, 1H), 10.5 (s, 1H).

Example 9: Synthesis of 8-bromo-2-chloro-5-fluoroquinoline-3-carbaldehyde 8-bromo-2-chloro-5-fluoroquinoline-3-carbaldehyde was prepared according to the procedures described in Example 8. $^1$H NMR (300 MHz, $CDCl_3$) δ 7.62 (d, J=8.7 Hz, 1H), 8.46 (d, J=6.9 Hz, 1H), 8.52 (d, J=8.7 Hz, 1H), 10.5 (s, 1H).

Biological Characterization of Exemplary Compounds

Exemplary compounds of the invention were tested for inhibitory activity or potency against BRD4 (BD1) and BRD4 (BD2) using AlphaScreen FRET binding assay, and exemplary compounds of the invention were further tested for inhibitory activity or potency against class I PI3Ks (p110α/p85α, p110β/p85α, p110δ/p85α and p110γ) using a cell-free based PI3K HTRF assay. All assays were performed at Reaction Biology Corporation, One Great Valley Parkway, Suite 2, Malvern, Pa. 19355, USA.

Example 10: Inhibitory activity or potency against BRD4 (BD1) and BRD4 (BD2)

Exemplary compounds of the invention were tested for inhibitory activity or potency against BRD4 (BD1) and BRD4 (BD2) using AlphaScreen FRET binding assay. BRD4 (BD1; 17.8 kDa) used was recombinant human BRD4 (BD1; aa 44-170), which expressed in E. coli with N-terminal His-tag, and BRD4 (BD2; 15.7 kDa) used was recombinant human BRD4 (BD2; aa 349-460), which expressed in E. coli with N-terminal His-tag. Briefly, donor beads coated with streptavidin were incubated with biotinylated histone H4 peptide (residues 1-21) containing KAc (K5/8/12/16Ac). In the absence of inhibitor, the His-tagged reader domain of BRD4 binds to KAc-histone H4 peptide, thereby recruiting acceptor beads coated with a nickel chelator. Binding potential is assessed by detecting light emission (520-620 nm) from acceptor beads following laser excitation (680 nm) of a photosensitizer within the donor beads that converts ambient oxygen to singlet oxygen.

Exemplary compounds of the invention were tested their inhibitory activity or potency against BRD4 (BD1) and BRD4 (BD2) in 10-dose $IC_{50}$ mode with 3-fold serial dilution starting at 10 µM. The control compound, JQ-1, was tested in the same conditions. Table 4 below summarizes the $IC_{50}$ values that were collected against 2 Bromodomains for compounds exemplified in this invention. All $IC_{50}$ values were reported in unites of nM. An $IC_{50}$ value less than 0.0508 nM or 0.508 nM, or higher than 1 mM or 10 mM was estimated based on the best curve fitting available. Empty cells indicate no inhibition or compound activity that could not be fit to an $IC_{50}$ curve.

TABLE 4

| | $IC_{50}$ value (nM) for the nhibition of BRD4 (BD1) and BRD4 (BD7) | |
|---|---|---|
| Compound | BRD4 (BD1) | BRD4 (BD2) |
| 1 | | |
| 2 | | |
| 3 | | |
| 4 | 8000 | Not determined |
| 5 | $IC_{50}$ = JQ1: 38.5 nM | |
| 6 | 3.5 | Not setermined |
| | $IC_{50}$ = JQ1: 38.5 nM | |
| 7 | 694 | Not determined |
| | $IC_{50}$ = JQ1: 38.5 nM | |
| 8 | 28 | 7.7 |
| 9 | 9460 | Not determined |
| | $IC_{50}$ = JQ1: 38.5 nM | |
| 10 | 3980 | Not determined |
| | $IC_{50}$ = JQ1: 27.5 nM | |
| 11 | 24 | 86 |
| | $IC_{50}$ = JQ1: 27.5 nM | $IC_{50}$ = JQ1: 19.0 nM |
| 12 | 35 | Not determined |
| | $IC_{50}$ = JQ1: 27.5 nM | |
| 13 | 799 | 12.4 |
| 14 | >10000 | 4210 |
| 15 | 1250 | 680 |
| 16 | | 4970 |
| 17 | | 745 |
| 18 | 84.5 | 85.2 |
| 19 | 23.9 | 19.3 |
| 20 | 11.1 | 10,7 |
| 21 | 24.8 | 18.1 |
| 22 | 636 | 74.5 |

TABLE 4-continued

| | $IC_{50}$ value (nM) for the nhibition of BRD4 (BD1) and BRD4 (BD7) | |
|---|---|---|
| Compound | BRD4 (BD1) | BRD4 (BD2) |
| 23 | 26.7 | 12.9 |
| 24 | 12.5 | 9.07 |
| 25 | 55.3 | 20.7 |
| 26 | 11.8 | 24.1 |
| 27 | 2890 | 565 |
| 28 | 446 | 148 |
| 29 | 37.9 | 46.6 |
| 30 | 4060 | 1600 |
| JQ-1 | 64.1 | 24.4 |

Example 11: Inhibitory activity or potency against class I PI3Ks

Exemplary compounds of the invention were tested for inhibitory activity or potency against class I PI3Ks (p110α/p85α, p110β/p85α, p110δp85α and p110γ) using a cell-free based PI3K HTRF assay. This assay was used to detect the formation of the product 3,4,5-inositol triphosphate molecule (PIP3) by displacement of biotin-PIP3 from an energy transfer complex consisting of Europium labeled anti-GST monoclonal antibody, a GST-tagged pleckstrin homology (PH) domain, biotinylated PIP3 and Streptavidin-Allophycocyanin (APC). Excitation of Europium in the complex results in an energy transfer to the APC and a fluorescent emission at 665 nm. The PIPS product formed by human PI3-Kinase activity displaces biotin-PIP3 from the complex resulting in a loss of energy transfer and thus a decrease in signal.

Human class I PI3K isoforms were co-expressed in a Baculovirus infected cell expression system. The PI3K isoforms were assayed in the presence of HEPES (50 mM, pH 7.0), $NaN_3$ (0.02%), BSA (0.01%), orthovanadate (0.1 mM), and DMSO (1%). The exemplary compounds dissolved in DMSO were delivered into the kinase reaction mixture by Acoustic technology (Echo550; nanoliter range), and were pre-incubated for 10 min at room temperature before adding ATP (10 µM) to initiate the reaction. After 30 min at 30° C., the reactions were quenched with a stop solution, incubated overnight, with a detection mixture before measuring HTRF (Ex: 320 nm; Em: 615/665 nm). The emission ratio is converted into, µM PIP3 production based on PIP3 standard curves, and the nonlinear regression to obtain the standard curve and $IC_{50}$ values are performed using Graphpad Prism software.

Exemplary compounds of the invention were tested for their inhibitory activity or potency against PI3Kδ in 10-dose $IC_{50}$ mode with 3-fold, serial dilution starting at 10 pM, and exemplary compounds of the invention were tested for their inhibitory activity or potency against PI3Kα, PI3Kβ, and PI3Kγ in 10-dose $IC_{50}$ mode with 3-fold serial dilution starting at 1 µM. The control compound, PI-103, was tested with 3-fold serial dilution starting at 10 µM. Table 5 below, summarizes the $IC_{50}$ values that were collected against class I PI3Ks for compounds exemplified in this invention. All $IC_{50}$ values were reported in unites of nM. Empty cells indicate no inhibition or compound activity that could not be fit to an $IC_{50}$ curve.

TABLE 5

IC$_{50}$ value (nM) against PI3Kα, PI3Kβ, PI3Kδ and PI3Kγ

| Compound | PI3Kα | PI3Kβ | PI3Kδ | PI3Kγ |
|---|---|---|---|---|
| 1 | | | | |
| 2 | | | | |
| 3 | Not determined | Not determined | 0.523<br>IC$_{50}$ = 3.68 nM (PI-103) | Not determined |
| 4 | Not determined | Not determined | 0.66<br>IC$_{50}$ = 3.68 nM (PI-103) | Not determined |
| 5 | | | | |
| 6 | | | | |
| 7 | | | | |
| 8 | | | | |
| 9 | Not determined | Not determined | 3.25<br>IC$_{50}$ = 3.68 nM (PI-103) | Not determined |
| 10 | Not determined | Not determined | 30.5<br>IC$_{50}$ = 3.68 nM (PI-103) | Not determined |
| 11 | 247<br>IC$_{50}$ = 4.37 nM (PI-103) | 567<br>IC$_{50}$ = 9.71 nM (PI-103) | 5.34<br>IC$_{50}$ = 4.48 nM (PI-103) | 56.6<br>IC$_{50}$ = 72.0 nM (PI-103) |
| 12 | Not determined | Not determined | 5.0<br>IC$_{50}$ = 4.48 nM (PI-103) | Not determined |
| 13 | | | | >10000 |
| 14 | | | | |
| 15 | | | | |
| 16 | | | | |
| 17 | | | | >10000 |
| 18 | 4270 | 874 | 1.89 | 39.2 |
| 19 | 535 | 596 | 3.04 | 79.8 |
| 20 | 2350 | 2180 | 5.09 | 38.0 |
| 21 | 531 | 118 | 3.68 | 2.0 |
| 22 | 544 | 3550 | 19.3 | 171 |
| 23 | 153 | 191 | 0.73 | 13.0 |
| 24 | 18,2 | 53.9 | 0.938 | 1.43 |
| 25 | 20.5 | 43.3 | 1.98 | 16,7 |
| 26 | 307 | 265 | 2.13 | 5.18 |
| 27 | 75.8 | 85.9 | 0.575 | 4.49 |
| 28 | 1020 | 354 | 1.56 | 11.7 |
| 29 | 867 | 263 | 1.23 | 19.2 |
| 30 | 181 | 65.4 | 1.28 | 30.8 |
| PI-103 | 7.41 | 8.89 | 6..58 | 62.5 |

Dual inhibitors of class I PI3Ks and BRD4 are rare because class I PI3Ks and BRD4 are two structurally and functionally unrelated targets. Exemplary compounds 3 and 4 demonstrated that the compounds of the present invention interact with the acetyl-lysine (KAc) site of BRD4 independently of the PI3K hinge-binding moiety. As type 1 inhibitors targeting two divergent targets, they could be easily transformed to PI3K-inactive inhibitors (i.e., novel BRD inhibitors; e.g., compound 6 and 8) or inactive molecules (e.g., compound 13 and 16). The unexpected dual inhibitory activity or potency against both divergent targets is attributed to not only the unusual overall shape of the molecules of the present invention (as described in U.S. Pat. No. 9,637,488), but also the specific KAc-mimicking groups selected and their position incorporated into the quinoline ring. As demonstrated in Table 4 and 5, N-methylpyridone group and pyrrolopyridone group at the 8-position of the quinoline are required for dual inhibition of class I PI3Ks and BRD4, and optimal selection of $R_1$, $R_2$, $R_3$, X, and Y as defined herein are needed in order to bind favorably and selectively in the ATP-binding pocket of PI3Ks and to disrupt protein interaction networks between BET and KAc-modified proteins.

Therapeutic Uses and Pharmaceutical Compositions of Compounds of the Present Invention As discussed above, the present invention provides novel dual inhibitors of class I PI3Ks and BRDs, and thus the inventive compounds have useful pharmaceutical and medicinal properties. Many exemplary compounds of this invention exhibit significant inhibitory activity against both class I PI3Ks and BRD4 and therefore are of value in the treatment of a wide variety of clinical conditions (i.e., age-related diseases) that benefit from inhibition of MYC, and/or BRDs, and/or PI3Ks (e.g., a cellular proliferative disorder). Such disorders include, but are not limited to those such as autoimmune, inflammatory and allergic diseases, asthma, COPD, parasitic and/or viral infections, diabetes, and cancer.

Accordingly, in another aspect of the present invention, a compound of the present invention may be employed alone, pharmaceutical compositions are provided, which comprise any one of novel dual inhibitors described herein (or a prodrug, pharmaceutically acceptable salts or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with other therapeutic agents for the treatment of a disease or disorder susceptible to amelioration by inhibition of MYC and/or BRDs and/or PI3Ks, such as a hyperproliferative disorder (e.g., cancer). The therapeutic agents used in the combination therapy of the present invention are known to be useful in the treatment of respiratory diseases, allergic diseases, inflammatory or autoimmune diseases, function disorders and neurological disorders and pain, cardiovascular diseases, viral infection, metabolism/endocrine function disorders, bone marrow and organ transplant rejection, myelodysplastic syndrome, myeloproliferative disorders, cancer and hematologic malignancies, leukemia, lymphomas and solid tumors. The solid tumor is selected from the group consisting of pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors, bone cancer, and soft tissue sarcoma. In some embodiments, the solid tumor is selected from non-small cell lung cancer, small-cell lung cancer, colon cancer, CNS cancer, melanoma, ovarian cancer, renal cancer, prostate cancer, and breast cancer. In certain embodiments, additional therapeutic agents used in the combination therapy of the present invention may be an approved chemotherapeutic agent, or it may be any one of a number of agents undergoing approval in the Food and Drug Administration.

The above-identified methods of treatment are preferably carried out by administering a therapeutically effective amount of a compound of the present invention to a subject in need of treatment. Compounds of the present invention are potent dual inhibitors of class I PI3Ks and BRDs. The compounds are readily synthesized and can be administered by a variety of routes, including orally, transdermally, or by injection or inhalation. In some embodiments, it is administered orally.

The term "therapeutically effective amount" of a compound of the present invention or a pharmaceutically acceptable salt, isomer, prodrug, isotopiically-labeled derivate, or solvate thereof, means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of MYC, and/or BRDs, and/or class I PI3Ks, and/or PI3Kδ and/or PI3Kγ activity. The therapeutically effective amount may vary depending on the subject, and disease or condition being treated, the weight and age of the subject, the severity of the disease or condition, and the manner of administering, which can readily be determined by one or ordinary skill in the art.

This invention provides a pharmaceutical composition comprising a compound of this invention and a pharmaceutically acceptable carrier, diluent, or excipient therefor. As used herein, a pharmaceutically acceptable carrier or diluent refers to a carrier or diluent that does not cause significant irritation to an organism and does not abrogate the biological activity and properties of the administered compound. The pharmaceutical composition may further comprise one or more additional therapeutic agents selected based on emerging rational combination strategies as described in the literature.

A compound of the present invention can be administered orally, or by injection or inhalation, and the like. A compound of the present invention can be administered as the neat chemical, but it is typical, and preferable, to administer the compound in the form of a pharmaceutical composition or formulation. Accordingly, the present invention also provides pharmaceutical compositions that comprise a compound of the present invention and a biocompatible pharmaceutical carrier, adjuvant, or vehicle. The composition can include a compound of the present invention either as the sole active agent or in combination with other therapeutic agents mixed with an excipient or other pharmaceutically acceptable carriers. Carriers and other ingredients can be deemed pharmaceutically acceptable insofar as they are compatible with other ingredients of the formulation and not deleterious to the recipient thereof. Techniques for formulation and administration of pharmaceutical compositions can be found in Remington's Pharmaceutical Sciences, 18th Ed., Mack Publishing Co, Easton, Pa., 1990; and Modern Pharmaceutics, Marcel Dekker, Inc. 3rd Ed. (G. S. Banker & C. T. Rhodes, Eds.). The pharmaceutical compositions are formulated to contain suitable pharmaceutically acceptable carriers, and optionally can comprise excipients and auxiliaries that facilitate processing of the active compounds into preparations that can be used pharmaceutically. The mode of administration generally determines the nature of the carrier. The pharmaceutical compositions of the present invention can be manufactured using any conventional method, e.g., mixing, dissolving, granulating, dragee-making, levigating, emulsifying, encapsulating, entrapping, melt-spinning, spray-drying, or lyophilizing processes. An optimal pharmaceutical formulation can be determined by one of skill in the art depending on the route of administration and the desired dosage.

In certain embodiments, a compound of the present invention can be combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of the present invention such that they do not adversely affect each other. Such compounds are suitably present in combination in amounts that are effective for the purpose intended. In one embodiment, a composition of this invention comprises a compound of the present invention, in combination with one or more chemotherapeutic agents used in "targeted therapy" and conventional chemotherapy, or therapeutic antibodies and antibody drug conjugates. In a particular embodiment of anti-cancer therapy, a compound of this invention, or a stereoisomer, geometric isomer, tautomer, solvate, metabolite, isotopically-labeled derivate, pharmaceutically acceptable salt, or prodrug thereof, may be combined with other chemotherapeutic, hormonal or antibody agents, as well as combined with surgical therapy and radiotherapy. Combination therapies according to the present invention thus comprise, the administration of at least one compound of the present invention, or a stereoisomer, geometric isomer, tautomer, solvate, metabolite, pharmaceutically acceptable salt, isotopically-labeled derivate, or prodrug thereof, and the use of at least one other cancer treatment method. The amounts of the compound(s) of the present invention and the other pharmaceutically active chemotherapeutic agent(s) and the relative timings of administration will be selected in order to achieve the desired combined therapeutic effect.

It will be appreciated that the therapies employed may achieve a desired effect for the same disorder. Non-limiting examples of suitable one or more additional therapeutic, agents that can be combined with the novel dual inhibitors targeting both BRDs and PI3Ks of the present invention are disclosed herein. For example, additional therapeutic agents may be an immunomodulatory agent, anti-cancer agent or agent useful for restoring or activating the immune system. In one embodiment, the therapeutic agent is a tyrosine kinase inhibitor, a MEK inhibitor, a BRAF inhibitor, an autophagy inhibitor, a PARP inhibitor, a BCL-2 antagonist, a CDK4/CDK6 (and/or CDK9) inhibitor, an inhibitor of DNA synthesis and repair, an immune checkpoint inhibitor, a Janus kinase inhibitor, an agonist or antagonist of Wnt signaling pathway, or a toll-like receptor 7 or 9 agonist, to name a few.

It will also be appreciated that the therapies employed may achieve a desired effect for different effects (e.g., control of any adverse effects). In certain embodiments, the pharmaceutical compositions of the present invention comprise one or more additional therapeutically active ingredients (e.g., palliative). For the purpose of the invention, the term "palliative" refers to treatment that is focused on the relief of symptoms of a disease and/or side effects of a therapeutic regimen. Non-limiting examples of additional therapeutic agent is corticosteroids, budesonide, an anti-TNF-α antibody (e.g., infliximab), a α4β7 gut homing integrin inhibitor (e.g., vedolizumab), a monoclonal antibody against IL-23p40 (e.g., ustekinumab), to name a few.

For a more comprehensive list of additional therapeutic agents, see the National Cancer Institute (NCI) website (www.nci.nih.gov) and the Food and Drug Administration (FDA) website (www.fda.gov). The combination therapy of the present invention may be administered as a simultaneous or sequential regimen. When administered sequentially, the combination may be, administered in two or more administrations. The combined administration includes co-administration, using separate formulations or a single pharmaceutical formulation, and consecutive administration in either order, wherein preferably there is a time period while both (or all) active agents simultaneously exert their biological activities.

Depending on the route of administration, a suitable dose can be calculated according to body weight, body surface area, or organ size. The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of any infection. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage, information and assays used, as well as the pharmacokinetic data observed in human clinical trials.

Another aspect of the present invention includes kits comprising a compound of this invention, a container, and optionally a package insert or label indicating a treatment. In one embodiment, the container may be a vial, jar, ampoule, preloaded syringe, or an intravenous bag. The term "package insert" refers to instructions customarily included in commercial packages of therapeutic products, that contain information about the indications, usage, dosage, administration, contraindications and/or warnings concerning the use of such therapeutic products. Suitable containers include, e.g., bottles, vials, syringes, blister pack, etc. The container may be formed from a variety of materials such as glass or plastic.

The invention and the manner and process of making and using it, are now described in such full, clear, concise, and exact terms as to enable any person skilled in the art to which it pertains, to make and use the same. All publications and patent documents cited in this specification are incorporated herein by reference for all that they disclose.

The invention claimed is:

1. A compound having the structure:

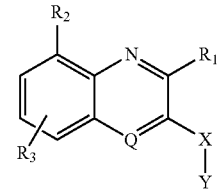

or a pharmaceutically acceptable, salt thereof, wherein:

X is selected from:

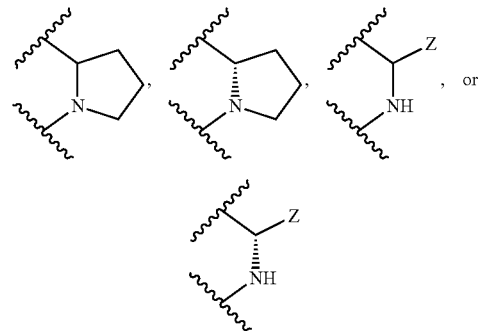

wherein: Z is hydrogen or small alkyl;

Q is C, or N;

$R_1$ is $NR_1^{II}R_1^{II}$, wherein $R_1^{I}$ and $R_1^{II}$ are independently selected from hydrogen, small alkyl, and/or $R_1^{I}$ and $R_1^{II}$ are taken together to form a $C_3$-$C_7$ cycloalkyl or $C_4$-$C_7$ heterocycloalkyl;

$R_2$ is selected from:

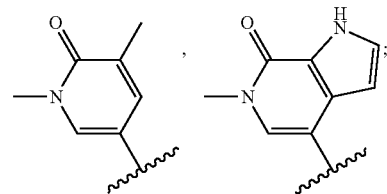

$R_3$ is hydrogen, or deuterium;

Y is selected from:

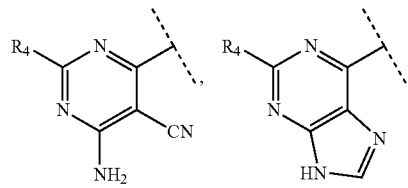

wherein: $R_4$ is independently selected from H, $NH_2$.

2. A compound having the structure:

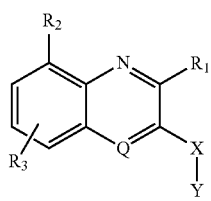

or a pharmaceutically acceptable salt thereof, wherein:
X is selected from:

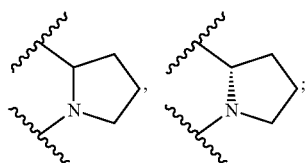 [SMILES: *C1CCCN1* ; *[C@@H]1CCCN1*]

Q is C, or N;
R₁ is 5- or 6-membered nitrogen-containing heteroaryl;
R₂ is selected from:

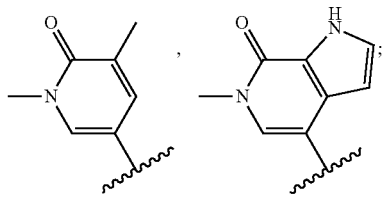

R₃ is hydrogen, or deuterium;
Y is selected from;

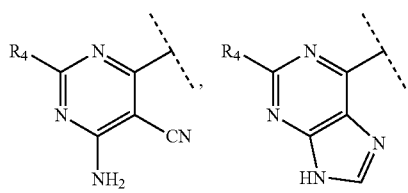

wherein: R₄ is independently selected from H, NH₂.

3. A compound of claims 1 and 2 or a pharmaceutically acceptable salt thereof, wherein the compound includes:

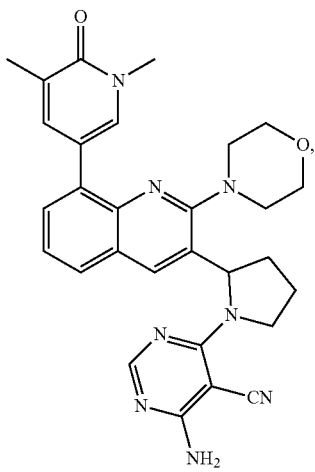

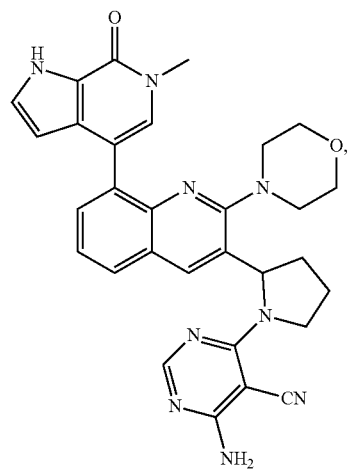

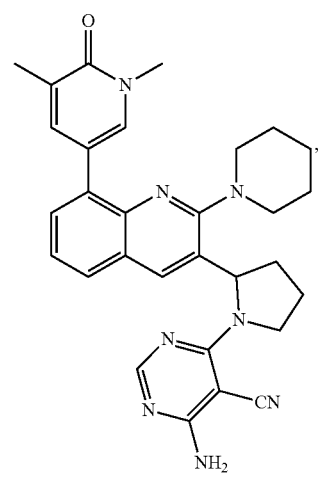

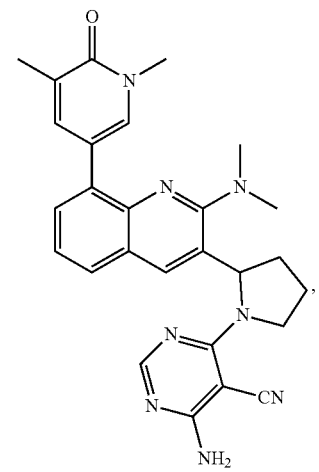

61
-continued
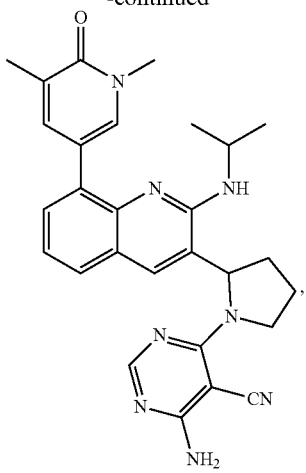
62
-continued
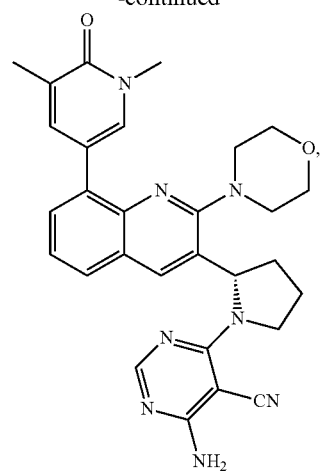
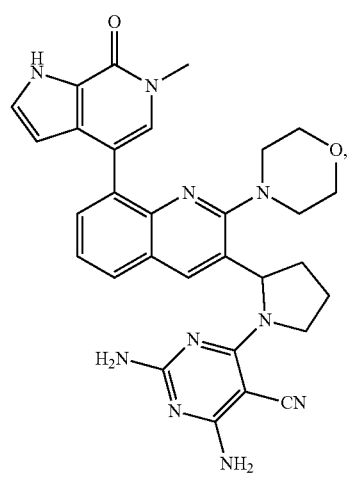
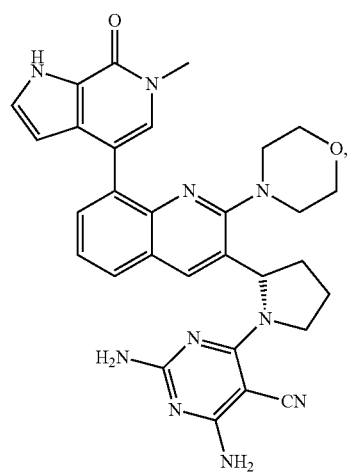
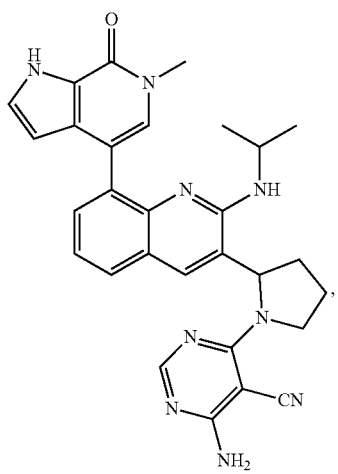
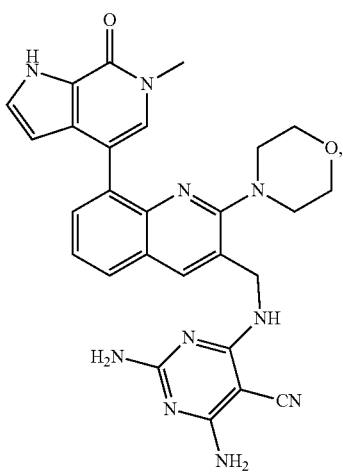

63
-continued
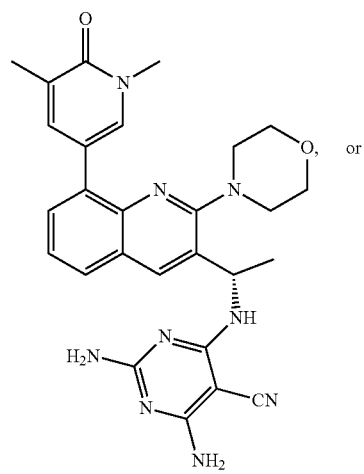
, or
64
-continued
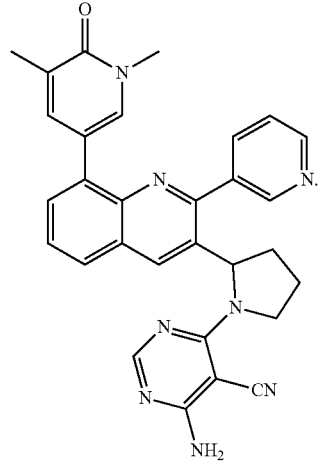
\* \* \* \* \*